United States Patent
Zhang et al.

(10) Patent No.: US 11,498,910 B2
(45) Date of Patent: Nov. 15, 2022

(54) COMPOUND, ORGANIC ELECTROLUMINESCENT DEVICE AND DISPLAY DEVICE

(71) Applicants: WUHAN TIANMA MICRO-ELECTRONICS CO., LTD., Wuhan (CN); WUHAN TIANMA MICROELECTRONICS CO., LTD. SHANGHAI BRANCH, Shanghai (CN)

(72) Inventors: Lei Zhang, Shanghai (CN); Wei Gao, Shanghai (CN); Wenpeng Dai, Shanghai (CN); Jinghua Niu, Shanghai (CN); Ping An, Shanghai (CN); Ying Liu, Shanghai (CN); Gaojun Huang, Shanghai (CN)

(73) Assignees: WUHAN TIANMA MICRO-ELECTRONICS CO., LTD., Wuhan (CN); WUHAN TIANMA MICROELECTRONICS CO., LTD. SHANGHAI BRANCH, Shanghai (CN)

( * ) Notice: Subject to any disclaimer, the term of this patent is extended or adjusted under 35 U.S.C. 154(b) by 401 days.

(21) Appl. No.: 16/586,987

(22) Filed: Sep. 29, 2019

(65) Prior Publication Data

US 2020/0024245 A1    Jan. 23, 2020

(30) Foreign Application Priority Data

Jun. 27, 2019 (CN) .......................... 201910570428.2

(51) Int. Cl.
*H01L 51/00* (2006.01)
*C07D 307/91* (2006.01)
(Continued)

(52) U.S. Cl.
CPC ......... *C07D 307/91* (2013.01); *C07D 239/26* (2013.01); *C07D 333/76* (2013.01);
(Continued)

(58) Field of Classification Search
None
See application file for complete search history.

(56) References Cited

U.S. PATENT DOCUMENTS

2017/0141325 A1* 5/2017 Lee ................... H01L 51/0072
2017/0186965 A1* 6/2017 Parham ............... H01L 51/0085
(Continued)

FOREIGN PATENT DOCUMENTS

CN      105315265 A      2/2016
CN      105899501 A      8/2016
(Continued)

*Primary Examiner* — Robert S Loewe
(74) *Attorney, Agent, or Firm* — Kilpatrick Townsend & Stockton LLP

(57) ABSTRACT

The disclosure relates to the field of organic electroluminescence technologies, in particular to a compound, an organic electroluminescent device and a display device. The compound has a structure as shown in Formula (I),

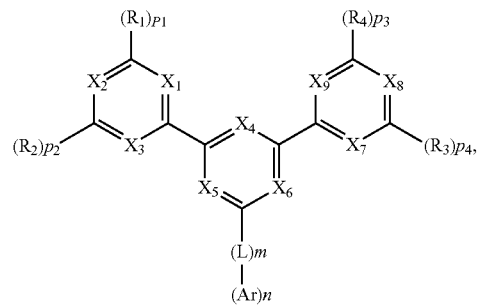

Formula (I)

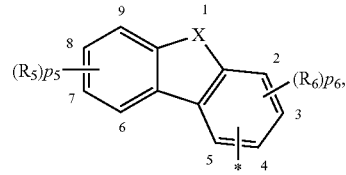

Formula (II)

wherein $X_1$-$X_9$ are each independently a C or N atom, and at least one of $X_1$-$X_9$ is an N atom; L is selected from substituted or unsubstituted C5-C40 aryl, and substituted or unsubstituted C3-C40 heteroaryl; Ar is For-
(Continued)

mula (II), wherein X is selected from an O or S atom; $R_1$-$R_6$ are each independently selected from substituted or unsubstituted C5-C40 aryl, and substituted or unsubstituted C3-C40 heteroaryl; $p_1$-$p_4$ are each independently selected from 0 or 1; $p_5$-$p_6$ are each independently selected from 0, 1, 2, or 3; m is selected from 0, 1, 2, or 3; n is selected from 1, 2, or 3; and * represents a connection site.

15 Claims, 1 Drawing Sheet

(51) Int. Cl.
 *C07D 333/76* (2006.01)
 *C07D 239/26* (2006.01)
 *H01L 51/50* (2006.01)
(52) U.S. Cl.
 CPC ...... *H01L 51/0067* (2013.01); *H01L 51/0073* (2013.01); *H01L 51/0074* (2013.01); *H01L 51/5072* (2013.01); *H01L 51/5096* (2013.01)

(56) References Cited

U.S. PATENT DOCUMENTS

| | | | |
|---|---|---|---|
| 2018/0337348 A1* | 11/2018 | Jung | C07F 7/0812 |
| 2019/0103560 A1* | 4/2019 | Jung | C07D 519/00 |
| 2019/0165282 A1* | 5/2019 | Parham | H01L 51/0034 |
| 2019/0198775 A1* | 6/2019 | Lui | H01L 51/0073 |
| 2019/0363260 A1* | 11/2019 | Han | C07D 409/10 |
| 2020/0095226 A1* | 3/2020 | Pan | C07D 401/10 |

FOREIGN PATENT DOCUMENTS

| | | | | |
|---|---|---|---|---|
| CN | 108884087 A | 11/2018 | | |
| CN | 110305110 A | 10/2019 | | |
| JP | 2014156441 A | 8/2014 | | |
| KR | 20150006758 A | 1/2015 | | |
| KR | 101959821 B1 | 3/2019 | | |
| TW | 201130805 A1 | 9/2011 | | |
| WO | WO-2018103749 A1 * | 6/2018 | ......... | H01L 51/0072 |

* cited by examiner

COMPOUND, ORGANIC ELECTROLUMINESCENT DEVICE AND DISPLAY DEVICE

CROSS REFERENCE TO RELATED APPLICATION

This disclosure claims the benefit and priority of Chinese Patent Application No. 201910570428.2, filed on Jun. 27, 2019. The entire disclosure of the above application is incorporated herein by reference.

FIELD

The disclosure relates to the field of organic electroluminescence technologies, in particular to a compound, an organic electroluminescent device and a display device.

BACKGROUND

Electron transport materials widely used at present, such as batho-phenanthroline (BPhen), bathocuproine (BCP) and TmPyPB, can generally meet the market demand of organic electroluminescent panels.

SUMMARY

The disclosure provides a compound, an organic electroluminescent device containing the compound, and a display device comprising the organic electroluminescent device.

According to one embodiment of the present disclosure, a compound is provided, and the compound has a structure as shown in Formula (I), Formula (I)

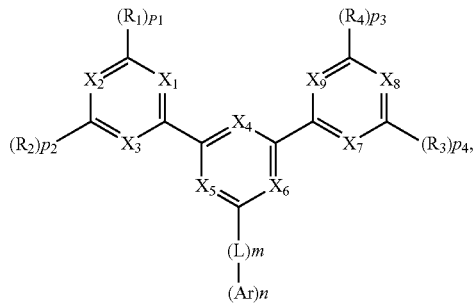

Formula (II)

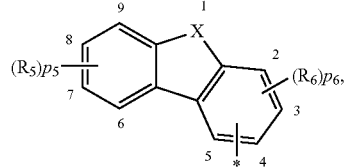

and $X_1$-$X_9$ are each independently a C or N atom, and at least one of $X_1$-$X_9$ is an N atom; L is selected from substituted or unsubstituted C5-C40 aryl, and substituted or unsubstituted C3-C40 heteroaryl;

Ar is Formula (II), and X is selected from an O or S atom; $R_1$-$R_6$ are each independently selected from substituted or unsubstituted C5-C40 aryl, and substituted or unsubstituted C3-C40 heteroaryl;

$p_1$-$p_4$ are each independently selected from 0 or 1; $p_5$-$p_6$ are each independently selected from 0, 1, 2, or 3;

m is selected from 0, 1, 2, or 3; n is selected from 1, 2, or 3; and

* represents a connection site.

According to another embodiment of the present disclosure, an organic electroluminescent device is provided, comprising a first electrode, a second electrode, and an organic functional layer located between the first electrode and the second electrode, the organic functional layer comprises an electron transport layer, and the electron transport material of the electron transport layer comprises the compound according to the present disclosure.

According to another embodiment of the present disclosure, a display device is provided, comprising the organic electroluminescent device according to the present disclosure.

DETAILED DESCRIPTION OF THE EMBODIMENTS

Figure 1:
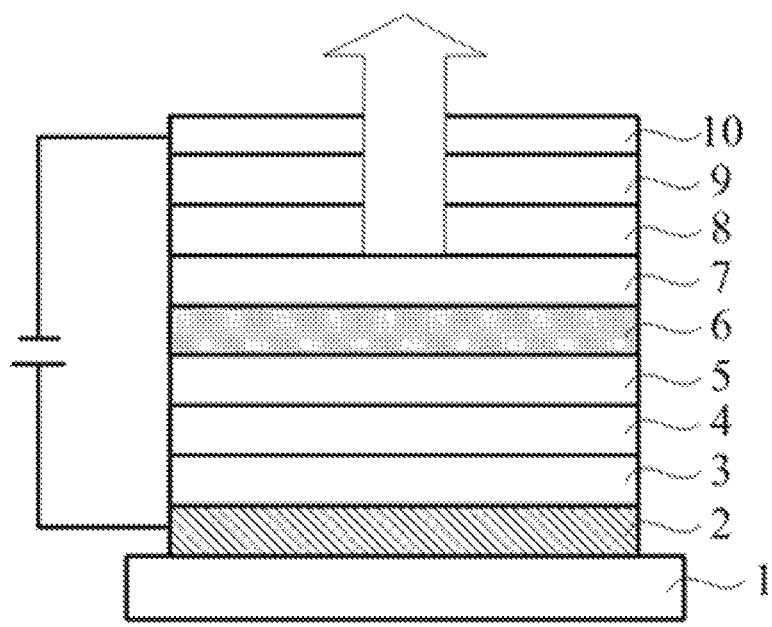
FIG. 1 is a structural diagram of an organic electroluminescent device according to the present disclosure.

The detailed embodiments are only for illustration of the present disclosure and do not constitute limitation on the content of the present disclosure. The present disclosure will be further illustrated and described with reference to specific embodiments.

The widely-used electron transport materials generally comply with the market demands of the organic electroluminescent panel, but their glass transition temperature is lower, generally less than 85° C. When the device runs, the resulting joule heat can result in degradation of the molecules and changes of the molecular structure, leading to lower efficiency and poorer thermal stability of the panel. At the same time, this molecular structure has very regular symmetry, and is easy to crystallize after a long time. Once the electron transport materials crystallize, the intermolecular charge transition mechanism is different from the amorphous film mechanism that functions well, resulting in the decrease of electron transport performance, the imbalance of electron and hole mobility rate of the whole device, and the great reduction of exciton formation efficiency. And the exciton formation is focused on the interface of the electron transport layer and light-emitting layer, leading to serious decrease of efficiency and lifetime of the device.

The disclosure provides a compound, an organic electroluminescent device containing the compound, and a display device comprising the organic electroluminescent device.

According to one embodiment of the present disclosure, a compound is provided, and the compound has a structure as shown in Formula (I), Formula (I)

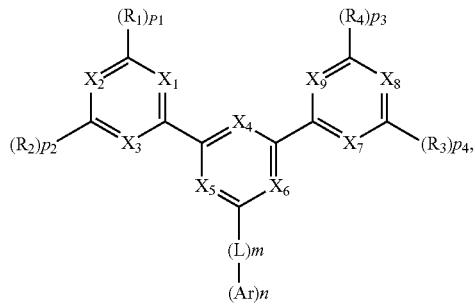

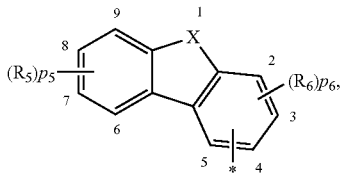

Formula (II)

and $X_1$-$X_9$ are each independently a C or N atom, and at least one of $X_1$-$X_9$ is an N atom; L is selected from substituted or unsubstituted C5-C40 aryl, and substituted or unsubstituted C3-C40 heteroaryl;

Ar is Formula (II), and X selected from is an O or S atom;

$R_1$-$R_6$ are each independently selected from substituted or unsubstituted C5-C40 aryl, and substituted or unsubstituted C3-C40 heteroaryl;

$p_1$-$p_4$ are each independently selected from 0 or 1; $p_5$-$p_6$ are each independently selected from 0, 1, 2, or 3;

m is selected from 0, 1, 2, or 3; n is selected from 1, 2, or 3; and

* represents a connection site.

According to one embodiment of the present disclosure, m is selected from 0 or 1.

According to one embodiment of the present disclosure, n is selected from 1.

According to one embodiment of the present disclosure, $p_1$-$p_6$ are each independently selected from 0 or 1.

In the present disclosure, "C5-C40 aryl" includes monocyclic aromatic hydrocarbon groups as well as fused polycyclic aromatic hydrocarbon groups, and may be selected from, for example, one or more of aromatic hydrocarbon groups selected from phenyl, biphenyl, 9,9-fluorenyl, benzene terphenyl, naphthyl, anthracyl, phenanthryl, 9,10-benzophenanthryl, 1,2-benzophenanthryl, acenaphthenyl, perylenyl, pyrenyl, indenyl, and the like.

"C3-C40 heteroaryl" may be selected from, for example, one or more of furyl, thienyl, pyrrolyl, oxazolyl, thiazolyl, pyrazolyl, pyranyl, imidazolyl, pyridyl, pyrazinyl, pyrimidinyl, 1,3,4-oxadiazolyl, 1,2,4-triazolyl, 1,3,5-triazinyl, indolyl, benzimidazolyl, dibenzofuranyl, dibenzothiophenyl, carbazolyl, quinolinyl, quinoxalinyl, phenanthrolinyl, phenazinyl, and pyridazinyl.

In the present disclosure, the substituent in the "substituted . . . " may be any one or more of C1-C10 alkyl or cycloalkyl, C2-C10 alkenyl, C1-C6 alkoxy, C6-C30 monocyclic aromatic hydrocarbon or fused polycyclic aromatic hydrocarbon groups, C3-C30 monocyclic heteroaromatic hydrocarbon or fused polycyclic heteroaromatic hydrocarbon groups.

In the present disclosure, when the value of m is greater than 1, that is, when the number of L is 2 or 3, the 2 or 3 Ls may be completely identical, completely different or only partially identical. Similarly, when the value of n is greater than 1, that is, when the number of Ar is 2 or 3, the 2 or 3 Ars may be completely identical, completely different or only partially identical. When the value of $p_5$ is greater than 1, that is, when the number of $R_5$ is 2 or 3, the 2 or 3 $R_5$s may be completely identical, completely different or only partially identical. When the value of $p_6$ is greater than 1, that is, when the number of $R_6$ is 2 or 3, the 2 or 3 $R_6$s may be completely identical, completely different or only partially identical.

The compound provided by the disclosure uses a nitrogen-containing aromatic heterocyclic ring as the mother ring in combination with a specific type of electron-donating group in use, so that the obtained compound has a proper HOMO value and a low LUMO value, and the electron transmission capability can be improved; the compound of the disclosure has low HOMO energy levels (all less than −6.0 eV), and can effectively block holes and limit the holes in a light emitting region, thereby realizing effective recombination of the holes and electrons; the compound of the disclosure has high triplet state energy levels (all of ET greater than 2.8 eV), and can effectively block the return of excitons and limit the excitons in the light emitting region, which is beneficial to widening the light emitting region, and improving the light emitting efficiency; the compound has high electron mobility, thus ensuring that the electrons and holes can be evenly recombined in a light emitting layer, and improving the generation rate of excitons; the compound has high glass transition temperature and thermal decomposition temperature, and the glass transition temperature is greater than 120° C., which can avoid the influence of joule heat generated during the operation of the device on the service life and efficiency of the device; the compound has excellent thin film stability and uniformity, and the degradation or attenuation induced by light scattering or crystallization is avoided; and the compound has high reduction potential, which facilitates the transmission of electrons.

The compound is used as the electron transport material of the organic electroluminescent device, and can effectively improve the electron migration capability of the device, thereby ensuring that the device has a high luminous efficiency, a long service life and a low driving voltage.

According to one embodiment of the present disclosure, at least one of $X_1$, $X_2$, $X_3$, $X_7$, $X_8$, and $X_9$ is an N atom.

The compound of the disclosure is an electron transport material, and at least one of $X_1$, $X_2$, $X_3$, $X_7$, $X_8$, and $X_9$ is an N atom, which can effectively ensure the electron-accepting capability of molecules, and ensure that molecules have high triplet states, and can be better matched with energy levels of adjacent layers.

According to one embodiment of the present disclosure, $X_1$ and $X_9$ are identical, $X_2$ and $X_8$ are identical, and $X_3$ and $X_7$ are identical. In this way, the symmetry of a molecular structure can be ensured, its synthesis is convenient to operate, the symmetrical structure can ensure the delocalization degree of the whole electron-accepting group, and the larger the delocalization degree, the easier the electrons migrate, thus improving the electron migration rate of the molecules.

According to one embodiment of the present disclosure, among $X_1$-$X_3$ and $X_7$-$X_9$, $X_2$ and $X_8$ are N atoms, and the others are C atoms.

When $X_2$ and $X_8$ are N atoms, the corresponding connected fragments are pyridyl groups, and at this time, the molecules have relatively high triplet energy levels, which can effectively block exciton transitions in red, green and blue light, improve the efficiency and service life of the device, and effectively adjust LUMO energy levels of the molecules.

According to one embodiment of the present disclosure, among $X_1$-$X_3$ and $X_7$-$X_9$, $X_2$, $X_3$, $X_7$, and $X_8$ are N atoms, and the others are C atoms.

When $X_2$, $X_3$, $X_7$, and $X_8$ are N atoms, the corresponding connected fragments are 4-pyrimidinyl groups, and at this time, the molecules have the highest triplet energy levels, which can effectively block exciton transitions in red, green and blue light, and improve the efficiency and service life of the device.

According to one embodiment of the present disclosure, among $X_1$-$X_3$ and $X_7$-$X_9$, $X_1$, $X_3$, $X_7$, and $X_9$ are N atoms, and the others are C atoms.

When $X_1$, $X_3$, $X_7$, and $X_9$ are N atoms, the corresponding connected fragments are 2-pyrimidinyl groups. Compared with the 4-pyrimidinyl groups, at this time, the molecules have relatively high triplet energy levels, which can effectively block exciton transitions in red and green light and improve the efficiency and service life of the device.

According to one embodiment of the present disclosure, among $X_4$-$X_6$, $X_4$ is an N atom, and $X_5$ and $X_6$ are C atoms.

Among $X_4$-$X_6$, when $X_4$ is an N atom, the electron-donating and electron-accepting groups of the molecules can be effectively separated, and the mutual influence of the electron-donating and electron-accepting groups between the molecules is small, so that the weaker electron-donating energy level of the molecules can be brought out to the maximum extent to effectively block the holes.

According to one embodiment of the present disclosure, among $X_4$-$X_6$, $X_4$ and $X_5$ are N atoms, and $X_6$ is a C atom.

Among $X_4$-$X_6$, when $X_4$ and $X_5$ are N atoms, the corresponding connected fragments are 4-pyrimidinyl groups, and at this time, the molecules have the highest triplet energy levels, which can effectively block exciton transitions in red, green and blue light, and improve the efficiency and service life of the device.

According to one embodiment of the present disclosure, among $X_4$-$X_6$, $X_5$ and $X_6$ are N atoms, and $X_4$ is a C atom.

Among $X_4$-$X_6$, when $X_5$ and $X_6$ are N atoms, at this time, the molecules are highly symmetrical, and its synthesis is convenient to operate.

According to one embodiment of the present disclosure, L is selected from any one of:

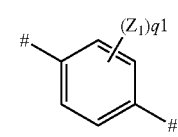

chemical formular 2-1

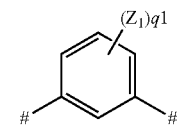

chemical formular 2-2

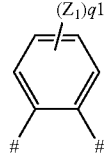

chemical formular 2-3

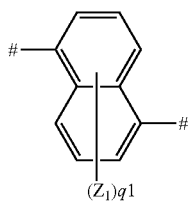

chemical formular 2-4

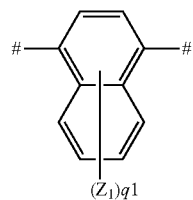

chemical formular 2-5

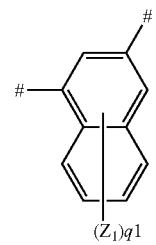

chemical formular 2-6

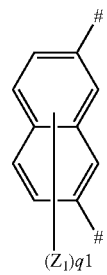

chemical formular 2-7

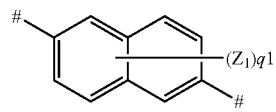

chemical formular 2-8

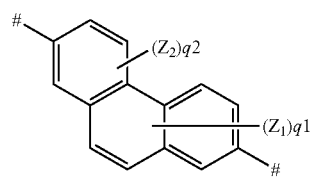

chemical formular 2-9

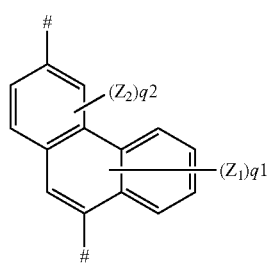

chemical formular 2-10

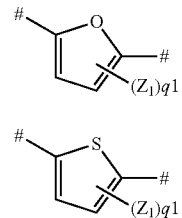

chemical formular 2-11 chemical formular 2-12 chemical formular 2-13

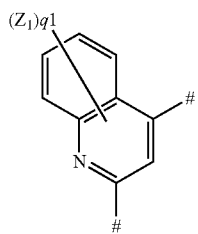

chemical formular 2-14

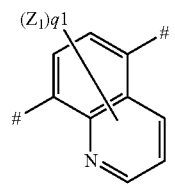

chemical formular 2-15

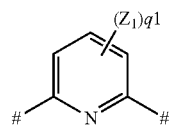

chemical formular 2-16

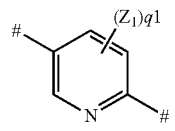

chemical formular 2-17

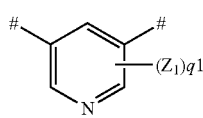

chemical formular 2-18

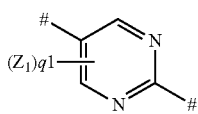

chemical formular 2-19

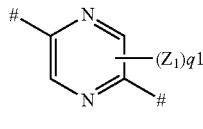

chemical formular 2-20

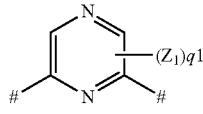

chemical formular 3-1

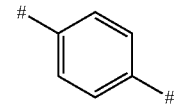

chemical formular 3-2

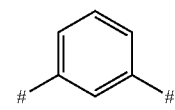

chemical formular 3-4

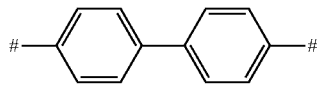

chemical formular 3-4

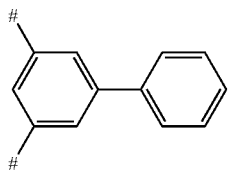

chemical formular 3-5

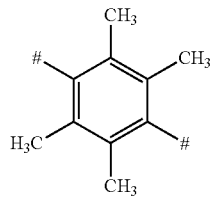

chemical formular 3-6

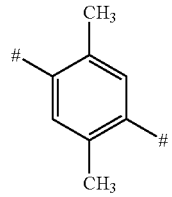

chemical formular 3-7

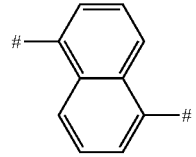

chemical formular 3-8

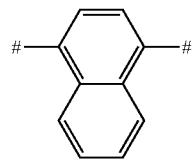

chemical formular 3-9

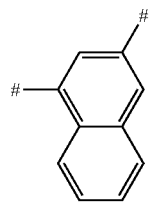

chemical formular 3-10

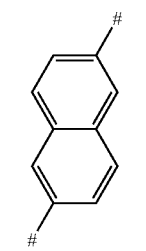

chemical formular 3-11 chemical formular 3-12

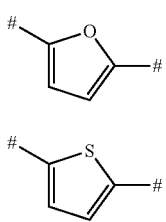

-continued chemical formular 3-13

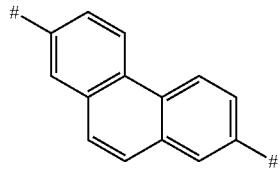

chemical formular 3-14

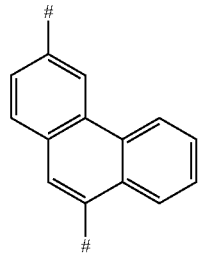

chemical formular 3-15

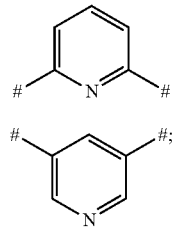

chemical formular 3-16

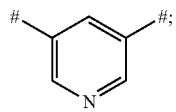

Z1 is selected from substituted or unsubstituted C5-C40 aryl, and substituted or unsubstituted C3-C40 heteroaryl;

q1 and q2 are each independently selected from 0, 1, or 2; and # represents a connection site.

In the two # positions shown in the L structure, L can be linked to the Ar group by any one of the # positions, as long as such a compound can be obtained by an appropriate preparation method.

According to one embodiment of the present disclosure, the Formula (II) is selected from any one of,

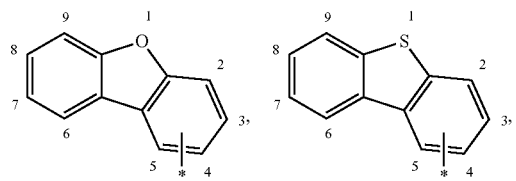

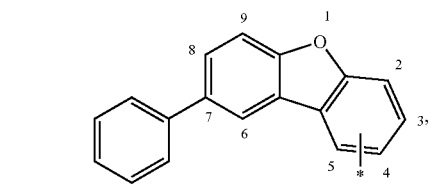

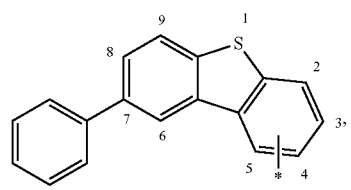

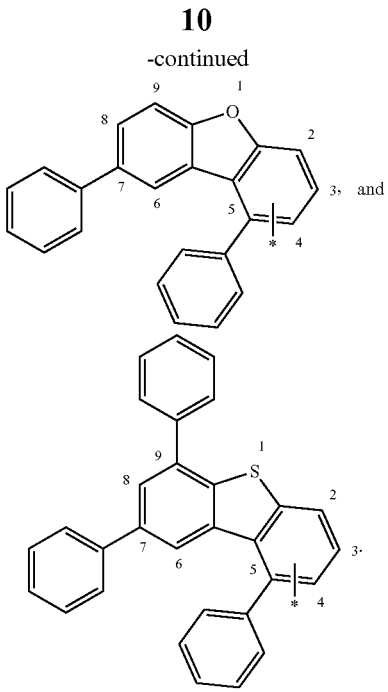

According to one embodiment of the present disclosure, the Formula (II) is selected from any one of

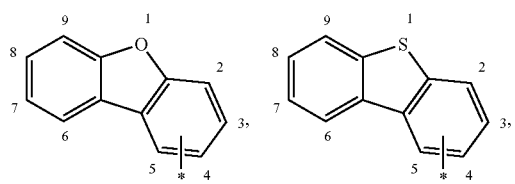

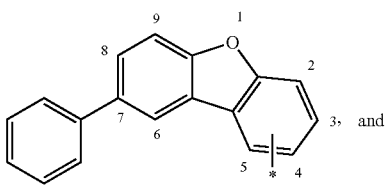

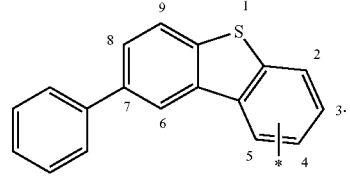

According to one embodiment of the present disclosure, the connection site * in the Formula (II) is the position of the No. 3 carbon atom, the No. 4 carbon atom, the No. 5 carbon atom, the No. 6 carbon atom, the No. 7 carbon atom, or the No. 8 carbon atom.

When the connection site * is the No. 3 carbon atom or the No. 8 carbon atom, synthetic raw materials are most sufficient and synthesis is convenient. When the connection site * is the No. 4 carbon atom or the No. 7 carbon atom, at this time, the molecular structure has the highest triplet state energy levels. When the connection site * is the No. 5 carbon atom or the No. 6 carbon atom, at this time, the configuration of the molecules is the most distorted and the solubility of the molecules becomes better.

According to one embodiment of the present disclosure, the compound is selected from any one of HB001 to HB072.

According to one embodiment of the present disclosure, the compound is selected from any one of HB002, HB042, HB044, HB058, HB063, HB067, HB068, HB069, and HB072.

According to another embodiment of the present disclosure, an organic electroluminescent device is provided, comprising a first electrode, a second electrode, and an organic functional layer located between the first electrode and the second electrode, the organic functional layer comprises an electron transport layer, and an electron transport material of the electron transport layer comprises the compound according to the present disclosure.

According to one embodiment of the present disclosure, the organic functional layer further comprises a hole blocking layer, and an electron transport material of the hole blocking layer comprises the compound according to the present disclosure.

According to one embodiment of the present disclosure, the organic electroluminescent device comprises a substrate, an anode and a cathode which are oppositely disposed, and an organic functional layer located between the anode and the cathode, and the organic functional layer comprises an electron injection layer, an electron transport layer, a light emitting layer, a hole transport layer, and a hole injection layer.

As shown in FIG. 1, the organic electroluminescent device according to one embodiment of the present disclosure comprises a substrate 1, an ITO anode 2, a hole injection layer 3, a first hole transport layer 4, a second hole transport layer 5, a light emitting layer 6, a hole blocking layer 7, an electron transport layer 8, an electron injection layer 9, and a cathode 10 arranged in order.

The organic electroluminescent device can be a single light emitting layer or multiple light emitting layers.

In one embodiment, the substrate may use a substrate in a conventional organic electroluminescent device, such as glass or plastic. The anode may be made of a transparent and highly conductive material, such as indium tin oxide (ITO), indium zinc oxide (IZO), tin dioxide (SnO2), and zinc oxide (ZnO).

The hole injection material (HIM) of the hole injection layer is required to have high thermal stability (high Tg), and a small potential barrier with the anode, and be capable of forming a pinhole-free thin film by vacuum evaporation. The commonly used HIMs are aromatic polyamine compounds, mainly triarylamine derivatives.

A hole transport material (HTM) of the hole transport layers is required to have a high thermal stability (high Tg) and high hole transport capability, and a pinhole-free film can be formed by vacuum evaporation. The commonly used HTMs are aromatic polyamine compounds, mainly triarylamine derivatives.

The organic light emitting layer comprises a host material and a guest material, and the guest material is a luminescent material, such as dyes, and the host material is required to have the following characteristics: having a reversible electrochemical redox potential, an HOMO energy level and LUMO energy level matched with the adjacent hole transport layer and electron transport layer, good and matched hole and electron transport capability, high thermal stability and good film forming properties, suitable singlet or triplet energy gaps for controlling excitons in the light emitting layer, as well as good energy transfer between corresponding fluorescent dyes or phosphorescent dyes. The luminescent material of the organic light emitting layer, taking dyes as an example, is required to have the following characteristics: having high fluorescence or phosphorescence quantum efficiency; the absorption spectrum of the dyes well overlapped with the emission spectrum of the main body, that is, the main body and the dyes are matched in terms of energy, and energy can be effectively transferred from the main body to the dyes; the emission peaks of red, green and blue light as narrow as possible to obtain good color purity; and high stability to make the vapor deposition possible.

An electron transport material (ETM) of the electron transport layer is required to have a reversible and high enough electrochemical reduction potential; an appropriate HOMO energy level and LUMO (Lowest Unoccupied Molecular Orbital) energy level, which enable electrons to be better injected, and preferably have hole blocking capability; and high electron transport capability, good film forming properties and high thermal stability. ETM is generally an aromatic compound with a conjugated plane of an electron-deficient structure. The electron transport layer adopts Alq3 (8-hydroxyquinoline aluminum) or TAZ (3-phenyl-4-(1'-naphthyl)-5-phenyl-1,2,4-triazole) or TPBi (1,3,5-tris(N-phenyl-2-benzimidazolyl)benzene) or a combination of any two selected from the three materials.

In the present disclosure, a manufacturing process of the organic electroluminescent device is as follows: the anode (the first electrode) is formed on a transparent or opaque smooth substrate, the organic functional layer is formed on the anode, and the cathode (the second electrode) is formed on the organic functional layer. The organic functional layer can be formed by known film forming methods such as evaporation, sputtering, spin coating, dipping, and ion plating.

According to another embodiment of the present disclosure, a display device is provided, comprising the organic electroluminescent device according to the present disclosure.

Figure 2:
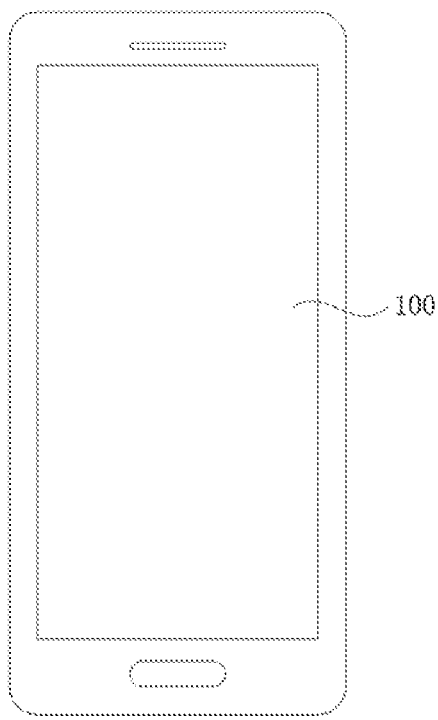
FIG. 2 is a schematic diagram of a display screen of a mobile phone.

According to one embodiment of the present disclosure, the display device may be a mobile phone, a computer, a liquid crystal television, a smart watch, a smart car, a VR or AR helmet, etc. There is no special restriction on this in the present disclosure. FIG. 2 is a schematic diagram of a mobile phone display screen, and 100 denotes a display screen.

Thus, it can be seen that there are many optional factors for the compound, organic electroluminescent device and display device according to the present disclosure, and different embodiments can be combined according to the claims of the present disclosure. The embodiments of the present disclosure are only intended as a specific description of the present disclosure, and are not intended to limit the present disclosure. The present disclosure will be further described below by taking the organic electroluminescent device containing the compound of the present disclosure as an embodiment.

Preparation Example 1 Synthesis of Compound HB002

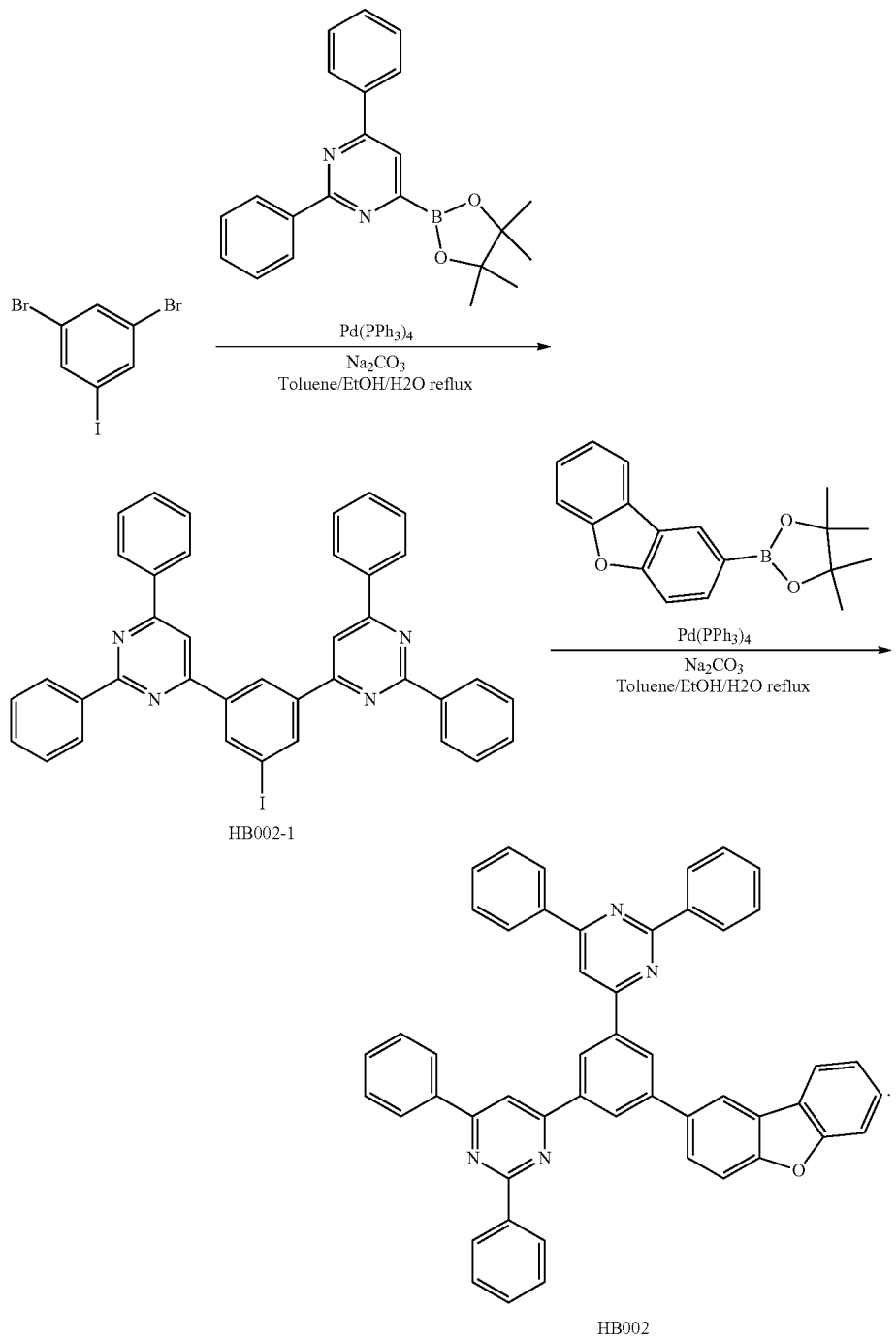

In a 250 mL round-bottom flask, 2,6-dibromo-4-iodobenzene (10 mmol), 2,4-diphenyl-6-(4,4,5,5-tetramethyl-1,3,2-dioxaborolan-2-yl)-pyrimidine (21 mmol) and Pd(PPh$_3$)$_4$ (0.3 mmol) are added to a mixture of toluene (30 mL)/ethanol (20 mL) and a potassium carbonate (12 mmol) aqueous solution (10 mL), and a reflux reaction is carried out in a nitrogen atmosphere for 12 hours. The obtained mixture is cooled to room temperature, added to water, and then filtered through a diatomite mat; the filtrate is extracted with dichloromethane, then washed with water, and dried with anhydrous magnesium sulfate; and after filtering and evaporating, the crude product is purified through silica gel column chromatography to obtain intermediate product HB002-1.

In a 250 mL round-bottom flask, the intermediate product HB002-1 (10 mmol), 3-(4,4,5,5-tetramethyl-1,3,2-dioxaborolan-2-yl)-dibenzofuran (10 mmol) and Pd(PPh$_3$)$_4$ (0.3 mmol) are added to a mixture of toluene (30 mL)/ethanol (20 mL) and a potassium carbonate (12 mmol) aqueous solution (10 mL), and a reflux reaction is carried out in a nitrogen atmosphere for 12 hours. The obtained mixture is cooled to room temperature, added to water, and then filtered through a diatomite mat; the filtrate is extracted with dichloromethane, then washed with water, and dried with anhydrous magnesium sulfate; and after filtering and evaporating, the crude product is purified through silica gel column chromatography to obtain final product HB002.

Element analysis structure of the compound HB002 (molecular formula of $C_{50}H_{32}N_4O$): theoretical values: C, 85.20; H, 4.58; N, 7.95; O, 2.27. Test values: C, 85.20; H, 4.59; N, 7.94; O, 2.27. ESI-MS(m/z)(M+) obtained by liquid chromatograph-mass spectrometry analysis: theoretical value: 704.26; test value: 704.82.

Preparation Example 2 Synthesis of Compound HB042

In a 250 mL round-bottom flask, 2,6-dibromo-4-iodobenzene (10 mmol), 4,6-diphenyl-2-(4,4,5,5-tetramethyl-1,3,2-dioxaborolan-2-yl)-pyrimidine (21 mmol) and $Pd(PPh_3)_4$ (0.3 mmol) are added to a mixture of toluene (30 mL)/ethanol (20 mL) and a potassium carbonate (12 mmol) aqueous solution (10 mL), and a reflux reaction is carried out in a nitrogen atmosphere for 12 hours. The obtained mixture is cooled to room temperature, added to water, and then filtered through a diatomite mat; the filtrate is extracted with dichloromethane, then washed with water, and dried with anhydrous magnesium sulfate; and after filtering and evaporating, the crude product is purified through silica gel column chromatography to obtain intermediate product HB042-1.

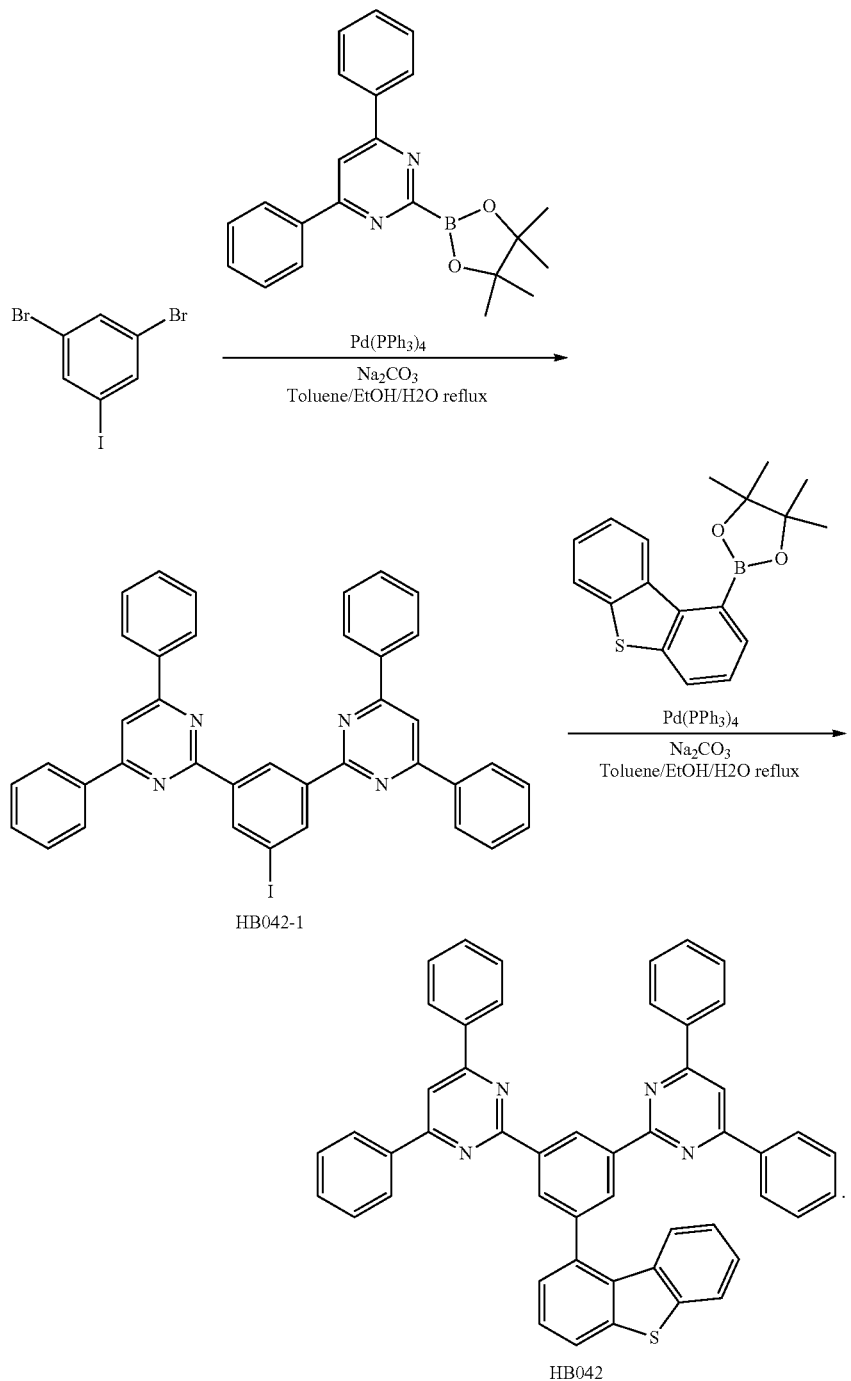

In a 250 mL round-bottom flask, the intermediate product HB042-1 (10 mmol), 4-(4,4,5,5-tetramethyl-1,3,2-dioxaborolan-2-yl)-dibenzothiophene (10 mmol) and Pd(PPh$_3$)$_4$ (0.3 mmol) are added to a mixture of toluene (30 mL)/ethanol (20 mL) and a potassium carbonate (12 mmol) aqueous solution (10 mL), and a reflux reaction is carried out in a nitrogen atmosphere for 12 hours. The obtained mixture is cooled to room temperature, added to water, and then filtered through a diatomite mat; the filtrate is extracted with dichloromethane, then washed with water, and dried with anhydrous magnesium sulfate; and after filtering and evaporating, the crude product is purified through silica gel column chromatography to obtain final product HB042.

Element analysis structure of the compound HB042 (molecular formula of $C_{50}H_{32}N_4S$): theoretical values: C, 83.31; H, 4.47; N, 7.77; S, 4.45. Test values: C, 83.30; H, 4.48; N, 7.77; S, 4.45. ESI-MS(m/z)(M+) obtained by liquid chromatograph-mass spectrometry analysis: theoretical value: 720.23; test value: 720.88.

Preparation Example 3 Synthesis of Compound HB044

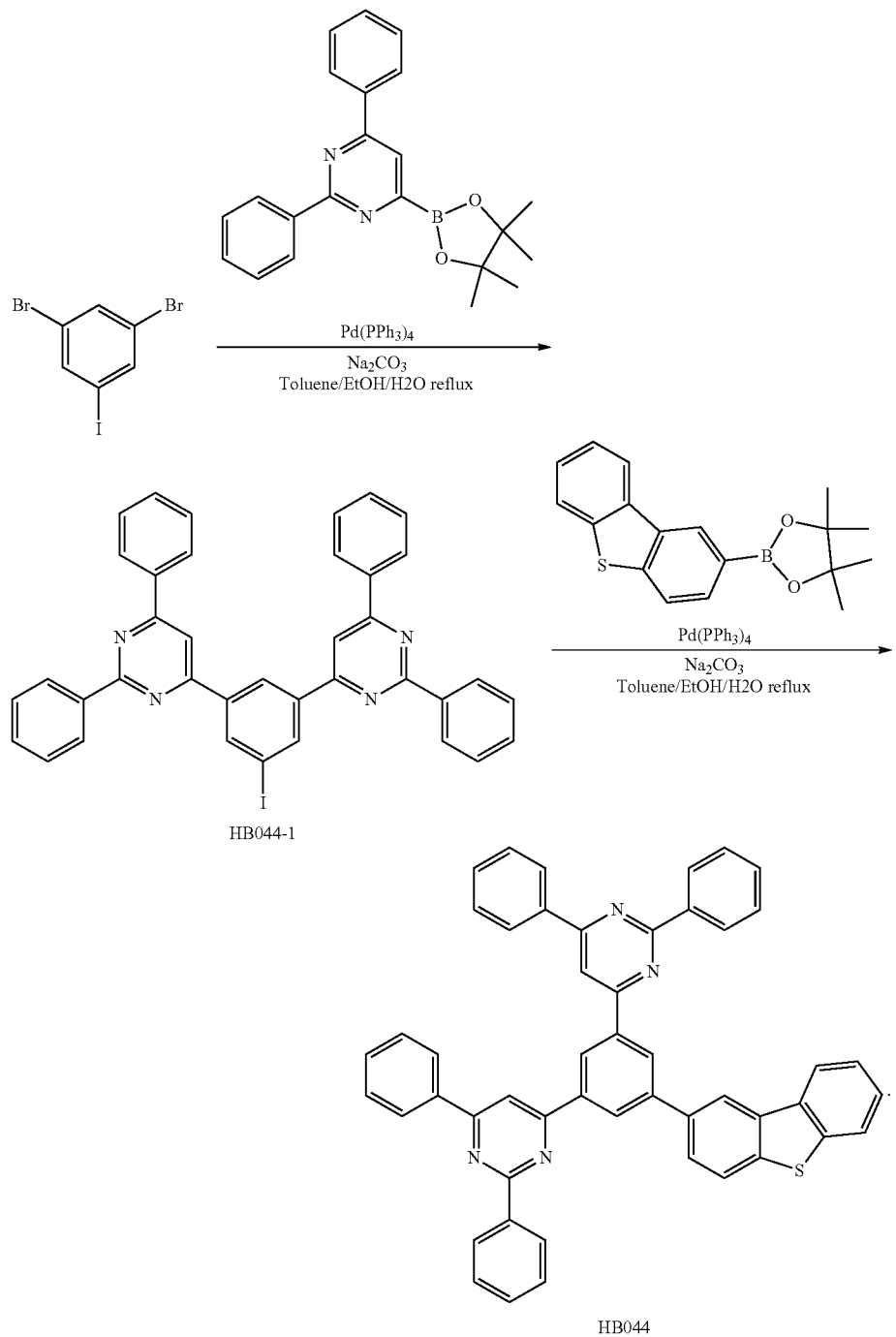

In a 250 mL round-bottom flask, 2,6-dibromo-4-iodobenzene (10 mmol), 2,4-diphenyl-6-(4,4,5,5-tetramethyl-1,3,2-dioxaborolan-2-yl)-pyrimidine (21 mmol) and Pd(PPh$_3$)$_4$ (0.3 mmol) are added to a mixture of toluene (30 mL)/ ethanol (20 mL) and a potassium carbonate (12 mmol) aqueous solution (10 mL), and a reflux reaction is carried out in a nitrogen atmosphere for 12 hours. The obtained mixture is cooled to room temperature, added to water, and then filtered through a diatomite mat; the filtrate is extracted with dichloromethane, then washed with water, and dried with anhydrous magnesium sulfate; and after filtering and evaporating, the crude product is purified through silica gel column chromatography to obtain intermediate product HB044-1.

In a 250 mL round-bottom flask, the intermediate product HB044-1 (10 mmol), 2-(4,4,5,5-tetramethyl-1,3,2-dioxaborolan-2-yl)-dibenzothiophene (10 mmol) and Pd(PPh$_3$)$_4$ (0.3 mmol) are added to a mixture of toluene (30 mL)/ethanol (20 mL) and a potassium carbonate (12 mmol) aqueous solution (10 mL), and a reflux reaction is carried out in a nitrogen atmosphere for 12 hours. The obtained mixture is cooled to room temperature, added to water, and then filtered through a diatomite mat; the filtrate is extracted with dichloromethane, then washed with water, and dried with anhydrous magnesium sulfate; and after filtering and evaporating, the crude product is purified through silica gel column chromatography to obtain final product HB044.

Element analysis structure of the compound HB044 (molecular formula of C$_{50}$H$_{32}$N$_4$S): theoretical values: C, 83.31; H, 4.47; N, 7.77; S, 4.45. Test values: C, 83.30; H, 4.48; N, 7.77; S, 4.45. ESI-MS(m/z)(M+) obtained by liquid chromatograph-mass spectrometry analysis: theoretical value: 720.23; test value: 720.88.

Preparation Example 4 Synthesis of Compound HB058

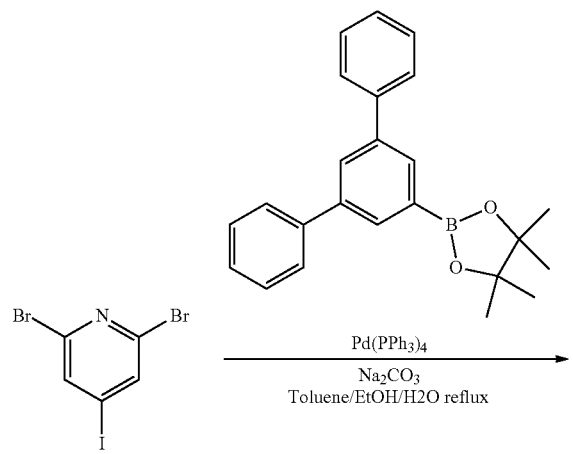

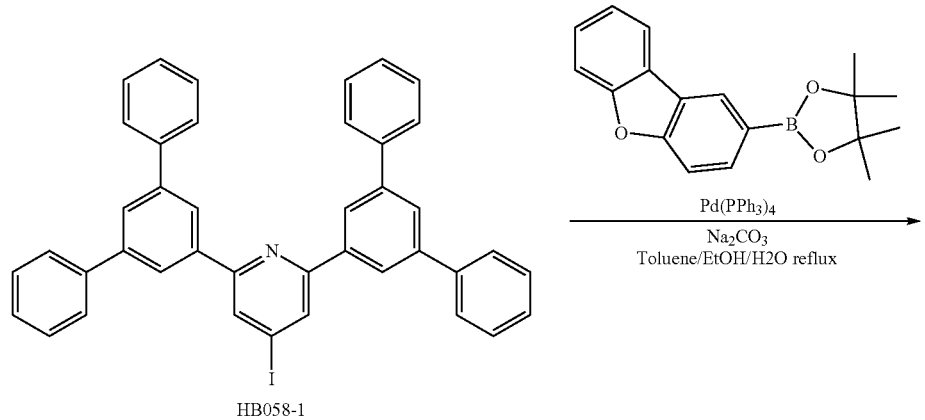

HB058-1

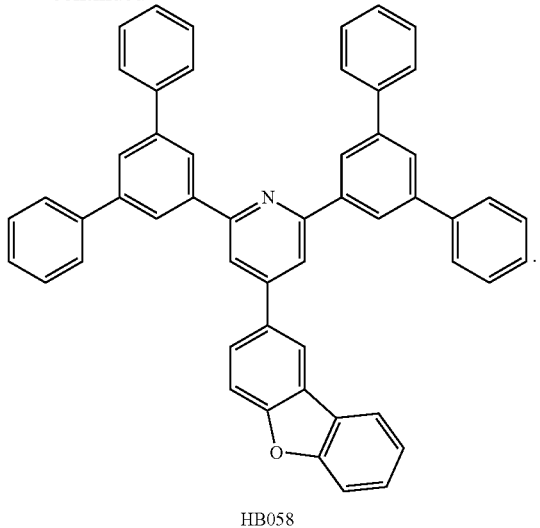

HB058

In a 250 mL round-bottom flask, 2,6-dibromo-4-iodopyridine (10 mmol) 3,5-diphenyl-1-(4,4,5,5-tetramethyl-1,3,2-dioxaborolan-2-yl)-benzene (21 mmol) and Pd(PPh$_3$)$_4$ (0.3 mmol) are added to a mixture of toluene (30 mL)/ethanol (20 mL) and a potassium carbonate (12 mmol) aqueous solution (10 mL), and a reflux reaction is carried out in a nitrogen atmosphere for 12 hours. The obtained mixture is cooled to room temperature, added to water, and then filtered through a diatomite mat; the filtrate is extracted with dichloromethane, then washed with water, and dried with anhydrous magnesium sulfate; and after filtering and evaporating, the crude product is purified through silica gel column chromatography to obtain intermediate product HB058-1.

In a 250 mL round-bottom flask, the intermediate product HB058-1 (10 mmol), 3-(4,4,5,5-tetramethyl-1,3,2-dioxaborolan-2-yl)-dibenzofuran (10 mmol) and Pd(PPh$_3$)$_4$ (0.3 mmol) are added to a mixture of toluene (30 mL)/ethanol (20 mL) and a potassium carbonate (12 mmol) aqueous solution (10 mL), and a reflux reaction is carried out in a nitrogen atmosphere for 12 hours. The obtained mixture is cooled to room temperature, added to water, and then filtered through a diatomite mat; the filtrate is extracted with dichloromethane, then washed with water, and dried with anhydrous magnesium sulfate; and after filtering and evaporating, the crude product is purified through silica gel column chromatography to obtain final product HB058.

Element analysis structure of the compound HB058 (molecular formula of $C_{53}H_{35}NO$): theoretical values: C, 90.70; H, 5.03; N, 2.00; O, 2.28. Test values: C, 90.71; H, 5.02; N, 2.00; O, 2.28. ESI-MS(m/z)(M+) obtained by liquid chromatograph-mass spectrometry analysis: theoretical value: 701.27; test value: 701.85.

Preparation Example 5 Synthesis of Compound HB063

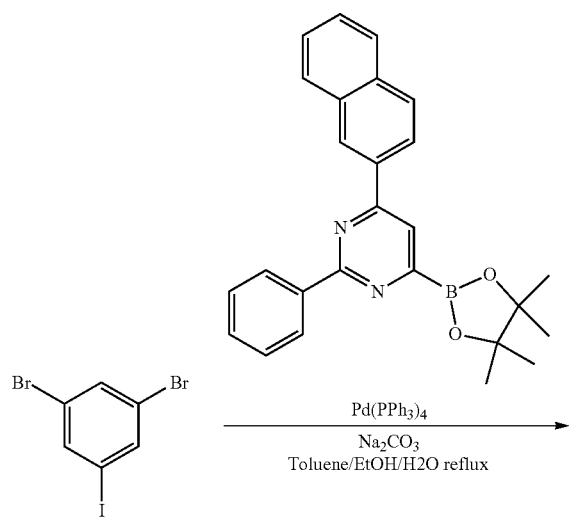

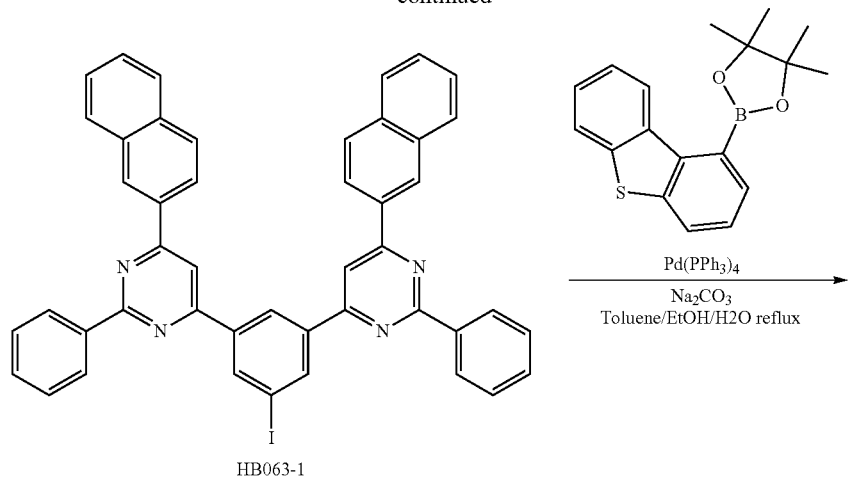

HB063-1

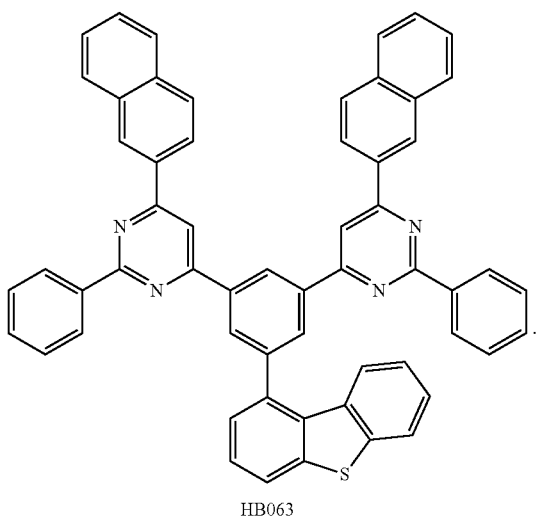

HB063

In a 250 mL round-bottom flask, 2,6-dibromo-4-iodobenzene (10 mmol), 2-phenyl-4-naphthyl-6-(4,4,5,5-tetramethyl-1,3,2-dioxaborolan-2-yl)-pyrimidine (21 mmol) and Pd(PPh$_3$)$_4$ (0.3 mmol) are added to a mixture of toluene (30 mL)/ethanol (20 mL) and a potassium carbonate (12 mmol) aqueous solution (10 mL), and a reflux reaction is carried out in a nitrogen atmosphere for 12 hours. The obtained mixture is cooled to room temperature, added to water, and then filtered through a diatomite mat; the filtrate is extracted with dichloromethane, then washed with water, and dried with anhydrous magnesium sulfate; and after filtering and evaporating, the crude product is purified through silica gel column chromatography to obtain intermediate product HB063-1.

In a 250 mL round-bottom flask, the intermediate product HB063-1 (10 mmol), 4-(4,4,5,5-tetramethyl-1,3,2-dioxaborolan-2-yl)-dibenzothiophene (10 mmol) and Pd(PPh$_3$)$_4$ (0.3 mmol) are added to a mixture of toluene (30 mL)/ethanol (20 mL) and a potassium carbonate (12 mmol) aqueous solution (10 mL), and a reflux reaction is carried out in a nitrogen atmosphere for 12 hours. The obtained mixture is cooled to room temperature, added to water, and then filtered through a diatomite mat; the filtrate is extracted with dichloromethane, then washed with water, and dried with anhydrous magnesium sulfate; and after filtering and evaporating, the crude product is purified through silica gel column chromatography to obtain final product HB063.

Element analysis structure of the compound HB063 (molecular formula of C$_{58}$H$_{36}$N$_4$S): theoretical values: C, 84.85; H, 4.42; N, 6.82; S, 3.91. Test values: C, 84.86; H, 4.41; N, 6.82; S, 3.91. ESI-MS(m/z)(M+) obtained by liquid chromatograph-mass spectrometry analysis: theoretical value: 820.27; test value: 821.00.

Preparation Example 6 Synthesis of Compound HB067

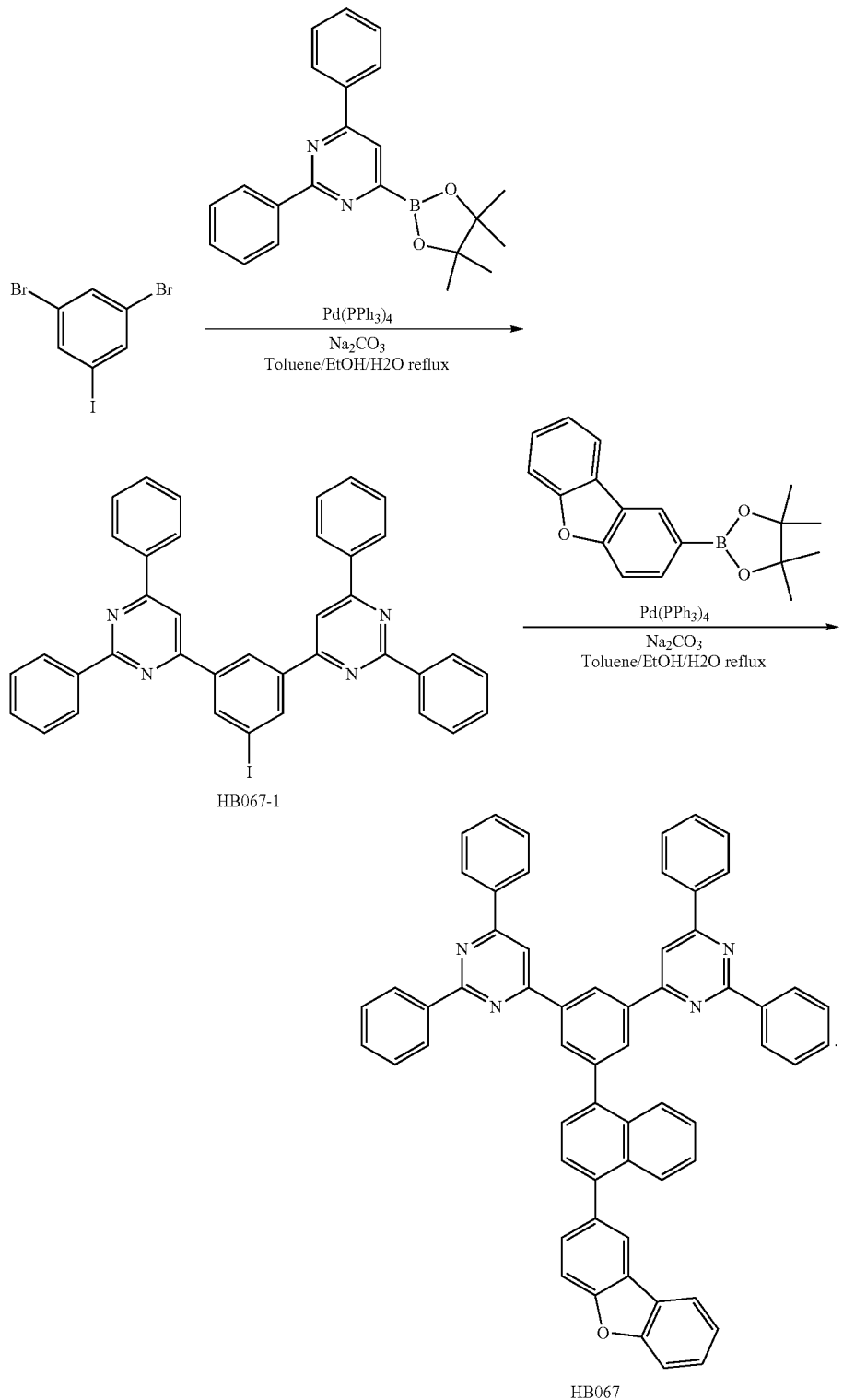

In a 250 mL round-bottom flask, 2,6-dibromo-4-iodobenzene (10 mmol), 2,4-diphenyl-6-(4,4,5,5-tetramethyl-1,3,2-dioxaborolan-2-yl)-pyrimidine (21 mmol) and Pd(PPh$_3$)$_4$ (0.3 mmol) are added to a mixture of toluene (30 mL)/ethanol (20 mL) and a potassium carbonate (12 mmol) aqueous solution (10 mL), and a reflux reaction is carried out in a nitrogen atmosphere for 12 hours. The obtained mixture is cooled to room temperature, added to water, and then filtered through a diatomite mat; the filtrate is extracted with dichloromethane, then washed with water, and dried with anhydrous magnesium sulfate; and after filtering and evaporating, the crude product is purified through silica gel column chromatography to obtain intermediate product HB067-1.

In a 250 mL round-bottom flask, the intermediate product HB067-1 (10 mmol), 2-(4-(4,4,5,5-tetramethyl-1,3,2-dioxaborolan-2-yl))-dibenzofuran (10 mmol) and Pd(PPh$_3$)$_4$ (0.3 mmol) are added to a mixture of toluene (30 mL)/ethanol (20 mL) and a potassium carbonate (12 mmol) aqueous solution (10 mL), and a reflux reaction is carried out in a nitrogen atmosphere for 12 hours. The obtained mixture is cooled to room temperature, added to water, and then filtered through a diatomite mat; the filtrate is extracted with dichloromethane, then washed with water, and dried with anhydrous magnesium sulfate; and after filtering and evaporating, the crude product is purified through silica gel column chromatography to obtain final product HB067.

Element analysis structure of the compound HB067 (molecular formula of $C_{60}H_{38}N_4O$): theoretical values: C, 86.72; H, 4.61; N, 6.74; O, 1.93. Test values: C, 86.72; H, 4.60; N, 6.75; O, 1.93. ESI-MS(m/z)(M+) obtained by liquid chromatograph-mass spectrometry analysis: theoretical value: 830.30; test value: 830.97.

Preparation Example 7 Synthesis of Compound HB068

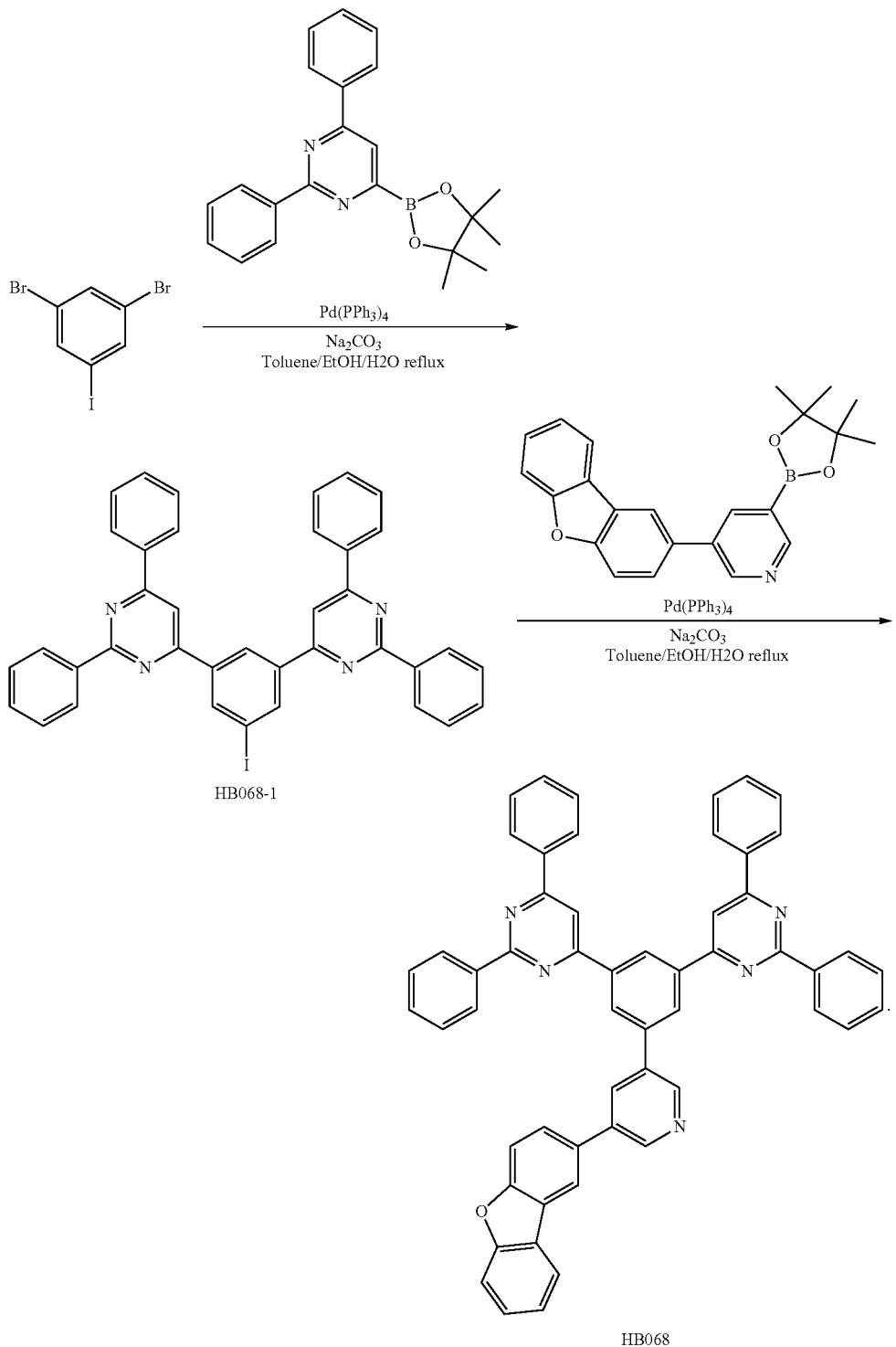

In a 250 mL round-bottom flask, 2,6-dibromo-4-iodobenzene (10 mmol), 2,4-diphenyl-6-(4,4,5,5-tetramethyl-1,3,2-dioxaborolan-2-yl)-pyrimidine (21 mmol) and Pd(PPh$_3$)$_4$ (0.3 mmol) are added to a mixture of toluene (30 mL)/ethanol (20 mL) and a potassium carbonate (12 mmol) aqueous solution (10 mL), and a reflux reaction is carried out in a nitrogen atmosphere for 12 hours. The obtained mixture is cooled to room temperature, added to water, and then filtered through a diatomite mat; the filtrate is extracted with dichloromethane, then washed with water, and dried with anhydrous magnesium sulfate; and after filtering and evaporating, the crude product is purified through silica gel column chromatography to obtain intermediate product HB068-1.

In a 250 mL round-bottom flask, the intermediate product HB068-1 (10 mmol), 3-(4,4,5,5-tetramethyl-1,3,2-dioxaborolan-2-yl)-5-dibenzofuranyl-pyridine (10 mmol) and Pd(PPh$_3$)$_4$ (0.3 mmol) are added to a mixture of toluene (30 mL)/ethanol (20 mL) and a potassium carbonate (12 mmol) aqueous solution (10 mL), and a reflux reaction is carried out in a nitrogen atmosphere for 12 hours. The obtained mixture is cooled to room temperature, added to water, and then filtered through a diatomite mat; the filtrate is extracted with dichloromethane, then washed with water, and dried with anhydrous magnesium sulfate; and after filtering and evaporating, the crude product is purified through silica gel column chromatography to obtain final product HB068.

Element analysis structure of the compound HB068 (molecular formula of $C_{55}H_{35}N_5O$): theoretical values: C, 84.49; H, 4.51; N, 8.96; O, 2.05. Test values: C, 84.49; H, 4.52; N, 8.95; O, 2.05. ESI-MS(m/z)(M+) obtained by liquid chromatograph-mass spectrometry analysis: theoretical value: 781.28; test value: 781.90.

Preparation Example 8 Synthesis of Compound HB069

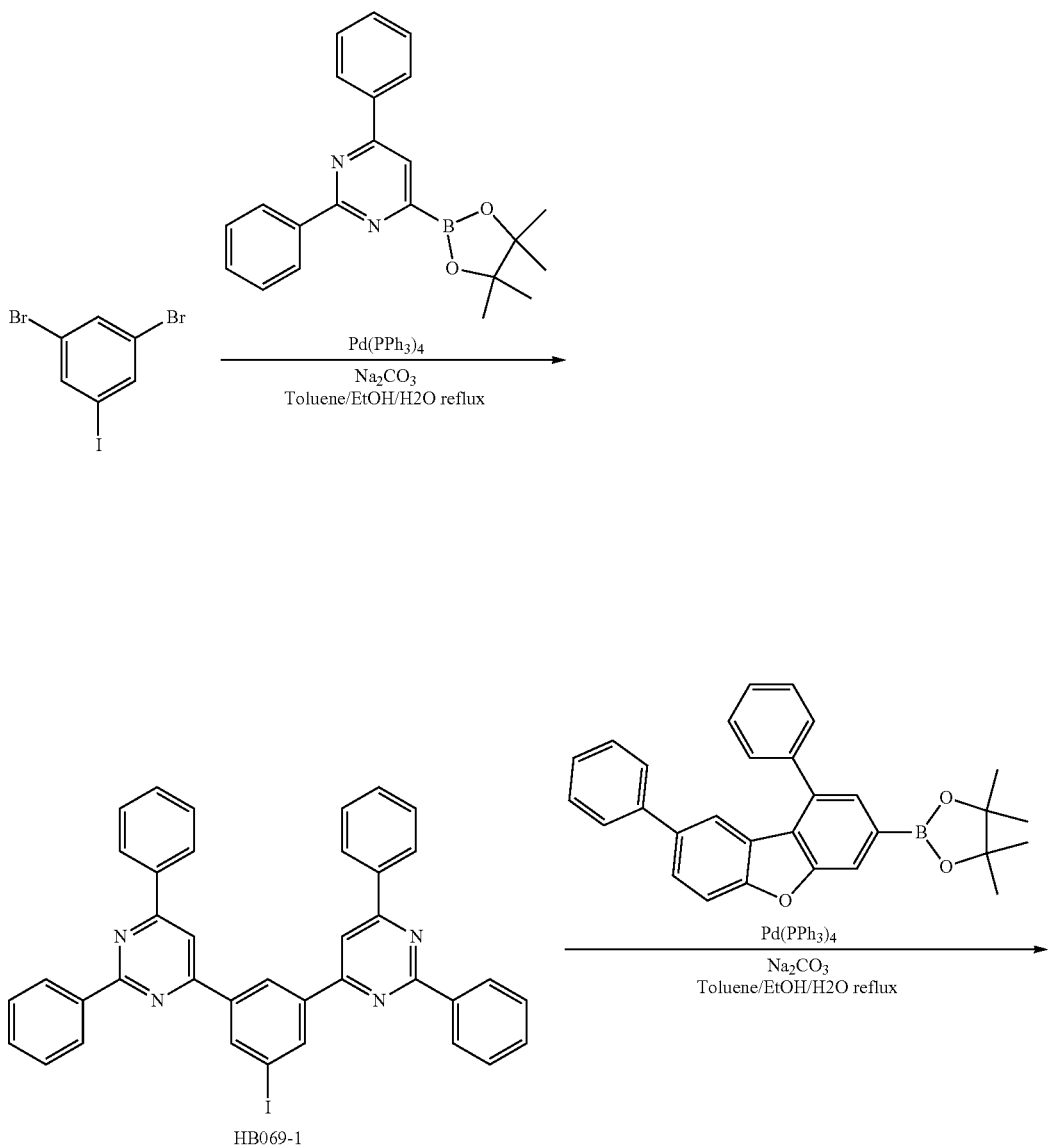

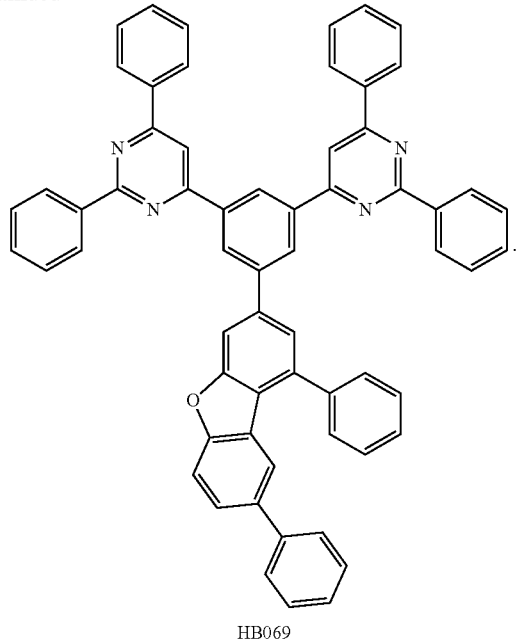

HB069

In a 250 mL round-bottom flask, 2,6-dibromo-4-iodobenzene (10 mmol), 2,4-diphenyl-6-(4,4,5,5-tetramethyl-1,3,2-dioxaborolan-2-yl)-pyrimidine (21 mmol) and Pd(PPh$_3$)$_4$ (0.3 mmol) are added to a mixture of toluene (30 mL)/ethanol (20 mL) and a potassium carbonate (12 mmol) aqueous solution (10 mL), and a reflux reaction is carried out in a nitrogen atmosphere for 12 hours. The obtained mixture is cooled to room temperature, added to water, and then filtered through a diatomite mat; the filtrate is extracted with dichloromethane, then washed with water, and dried with anhydrous magnesium sulfate; and after filtering and evaporating, the crude product is purified through silica gel column chromatography to obtain intermediate product HB069-1.

In a 250 mL round-bottom flask, the intermediate product HB069-1 (10 mmol), 3-(4,4,5,5-tetramethyl-1,3,2-dioxaborolan-2-yl)-1,8-diphenyl-dibenzofuran (10 mmol) and Pd(PPh$_3$)$_4$ (0.3 mmol) are added to a mixture of toluene (30 mL)/ethanol (20 mL) and a potassium carbonate (12 mmol) aqueous solution (10 mL), and a reflux reaction is carried out in a nitrogen atmosphere for 12 hours. The obtained mixture is cooled to room temperature, added to water, and then filtered through a diatomite mat; the filtrate is extracted with dichloromethane, then washed with water, and dried with anhydrous magnesium sulfate; and after filtering and evaporating, the crude product is purified through silica gel column chromatography to obtain final product HB069.

Element analysis structure of the compound HB069 (molecular formula of C$_{62}$H$_{40}$N$_4$O): theoretical values: C, 86.89; H, 4.70; N, 6.54; O, 1.87. Test values: C, 86.89; H, 4.70; N, 6.54; O, 1.87. ESI-MS(m/z)(M+) obtained by liquid chromatograph-mass spectrometry analysis: theoretical value: 856.32; test value: 856.92.

Preparation Example 9 Synthesis of Compound HB072

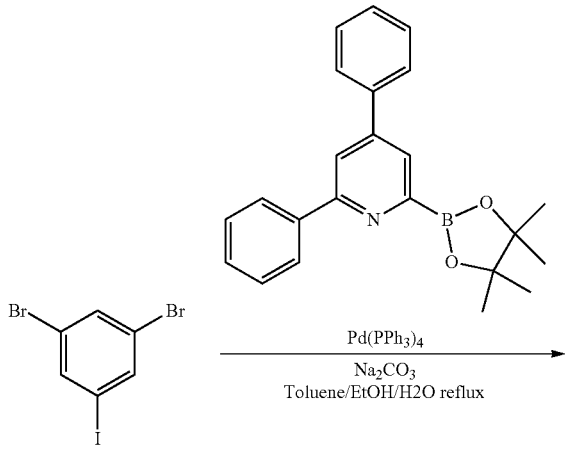

-continued

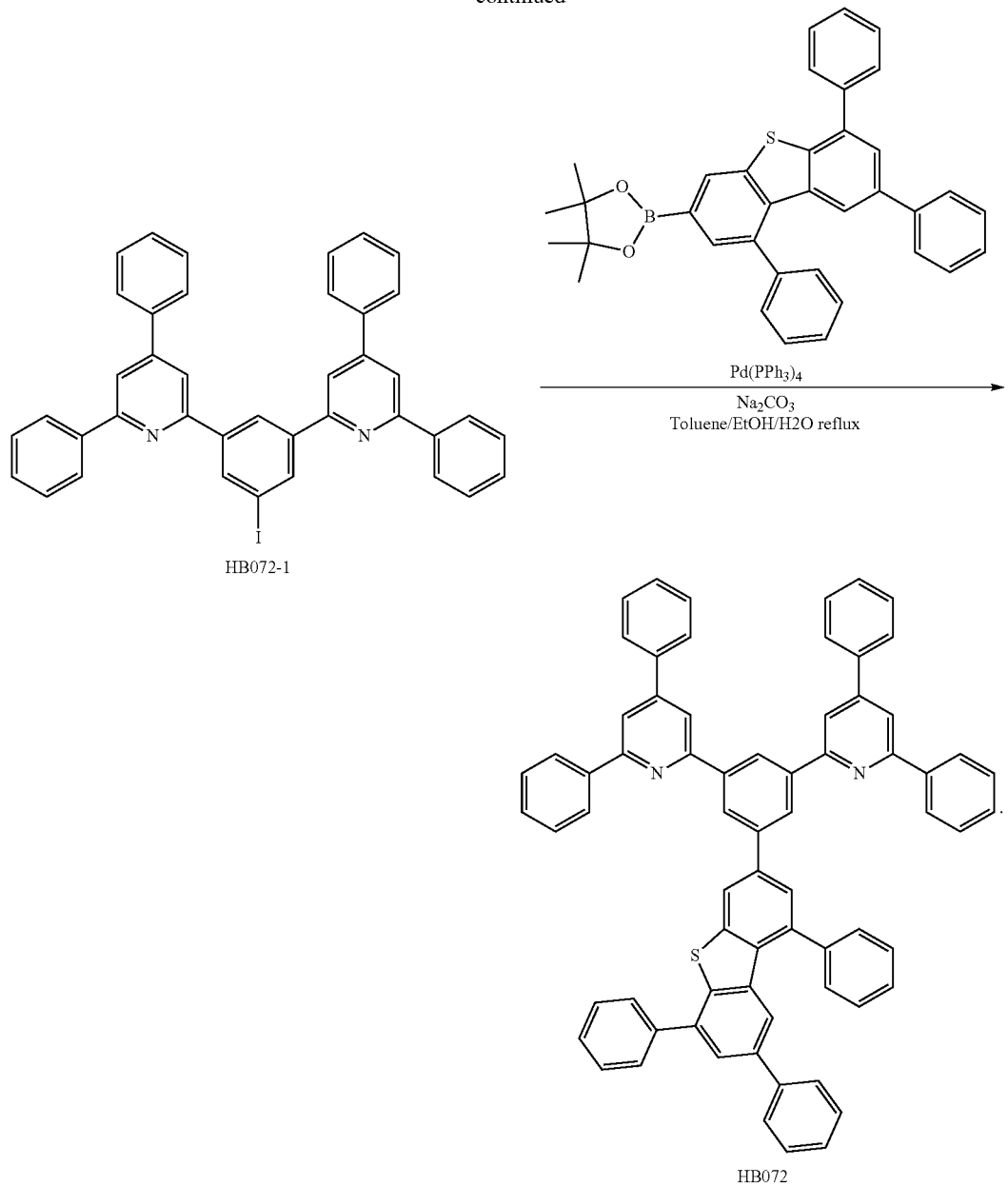

In a 250 mL round-bottom flask, 2,6-dibromo-4-iodobenzene (10 mmol), 4,6-diphenyl-2-(4,4,5,5-tetramethyl-1,3,2-dioxaborolan-2-yl)-pyridine (21 mmol) and Pd(PPh$_3$)$_4$ (0.3 mmol) are added to a mixture of toluene (30 mL)/ethanol (20 mL) and a potassium carbonate (12 mmol) aqueous solution (10 mL), and a reflux reaction is carried out in a nitrogen atmosphere for 12 hours. The obtained mixture is cooled to room temperature, added to water, and then filtered through a diatomite mat; the filtrate is extracted with dichloromethane, then washed with water, and dried with anhydrous magnesium sulfate; and after filtering and evaporating, the crude product is purified through silica gel column chromatography to obtain intermediate product HB072-1.

In a 250 mL round-bottom flask, the intermediate product HB072-1 (10 mmol), 3-(4,4,5,5-tetramethyl-1,3,2-dioxaborolan-2-yl)-1,5,7-triphenyl-dibenzothiophene (10 mmol) and Pd(PPh$_3$)$_4$ (0.3 mmol) are added to a mixture of toluene (30 mL)/ethanol (20 mL) and potassium carbonate (12 mmol) aqueous solution (10 mL), and a reflux reaction is carried out in a nitrogen atmosphere for 12 hours. The obtained mixture is cooled to room temperature, added to water, and then filtered through a diatomite mat; the filtrate is extracted with dichloromethane, then washed with water, and dried with anhydrous magnesium sulfate; and after filtering and evaporating, the crude product is purified through silica gel column chromatography to obtain final product HB072.

Element analysis structure of the compound HB072 (molecular formula of $C_{70}H_{46}N_2S$): theoretical values: C, 88.76; H, 4.90; N, 2.96; S, 3.39. Test values: C, 88.76; H, 4.91; N, 2.95; S, 3.39. ESI-MS(m/z)(M+) obtained by liquid chromatograph-mass spectrometry analysis: theoretical value: 946.34; test value: 946.98.

Other compounds are obtained by similar synthetic methods.

Performance Test.

(1) Simulated Calculation of the Compounds.

The singlet and triplet energy level difference of organic materials can be achieved by the software Guassian 09 (Guassian Inc.), and the specific simulation method of energy level difference ΔEst can be referred to J. Chem. Theory Comput., 2013, DOI: 10.1021/ct400415r. The optimization and excitation of a molecular structure can both be achieved by TD-DFT method "B3LYP" and a basis set "6-31g(d)", and Tg is measured by differential scanning calorimetry. In the present disclosure, simulated calculation is conducted on the compounds prepared in preparation examples 1-5 and the compound M selected in comparative example 1, and the results are shown in Table 1,

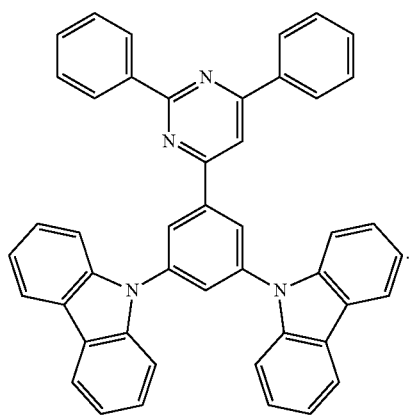

Structural formula of the compound M

TABLE 1

| Example Number | Compound Number | HOMO (eV) | LUMO (eV) | Eg (ev) | $E_T$ (eV) | Tg (° C.) |
|---|---|---|---|---|---|---|
| Example 1 | HB002 | −6.17 | −2.79 | 3.38 | 2.87 | 126° C. |
| Example 2 | HB042 | −6.06 | −2.72 | 3.32 | 2.80 | 120° C. |
| Example 3 | HB044 | −6.01 | −2.80 | 3.21 | 2.86 | 127° C. |
| Example 4 | HB058 | −6.13 | −2.74 | 3.39 | 2.82 | 124° C. |
| Example 5 | HB063 | −6.04 | −2.73 | 3.31 | 2.83 | 123° C. |
| Example 6 | HB067 | −6.04 | −2.73 | 3.31 | 2.83 | 123° C. |
| Example 7 | HB068 | −6.05 | −2.75 | 3.30 | 2.87 | 127° C. |
| Example 8 | HB069 | −6.09 | −2.78 | 3.31 | 2.80 | 123° C. |
| Example 9 | HB072 | −6.13 | −2.71 | 3.42 | 2.86 | 125° C. |
| Comparative Example 1 | M | −5.75 | −2.87 | 2.88 | 2.74 | 119° C. |

As can be seen from Table 1, the triplet energy levels of all compounds in the examples of the present disclosure are greater than 2.8 eV, which are higher than that of comparative example 1, and the glass transition temperatures are greater than 120° C., which are higher than that of comparative example 1. Meanwhile, for all the compounds in the examples of the present disclosure, HOMO energy levels are less than −6.0 eV and triplet energy levels are greater than 2.8 eV, so that the return of holes and excitons can be effectively blocked, the holes and excitons are limited in a light emitting region, the light emitting region is widened, and the light emitting efficiency and the service life of the device are improved.

(2) Performance of Organic Electroluminescent Device.

Example 10

This example provides an OLED display panel. As shown in FIG. 1, the OLED display panel comprises a substrate 1, an ITO anode 2, a hole injection layer 3, a first hole transport layer 4, a second hole transport layer 5, a light emitting layer 6, a hole blocking layer 7, an electron transport layer 8, an electron injection layer 9, and a cathode 10 (an aluminum electrode), and the thickness of the ITO anode 2 is 10 nm, and the thickness of the hole injection layer 3 is 5 nm; the thickness of the first hole transport layer 4 is 50 nm, and the thickness of the second hole transport layer 5 is 10 nm; and the thickness of the light emitting layer 6 is 20 nm, the thickness of the hole blocking layer 7 is 5 nm, the thickness of the electron transport layer 8 is 20 nm, the thickness of the electron injection layer 9 is 1 nm, and the thickness of the aluminum electrode 10 is 15 nm.

The preparation steps of the OLED display panel are as follows:

1) cutting the glass substrate 1 into a size of 50 mm*50 mm*0.7 mm, conducting ultrasonic treatment in isopropyl alcohol and deionized water for 30 minutes respectively, then exposing to ozone for about 10 minutes for cleaning, and mounting the obtained glass substrate with the ITO anode 2 on a vacuum deposition equipment;

2) vacuum-evaporating a material of the hole injection layer on the ITO anode layer 2 under a vacuum degree of $2\times10^{-6}$ Pa, and the material is HAT-CN with a thickness of 5 nm, and the layer is used as the hole injection layer 3;

3) vacuum-evaporating a material of the first hole transport layer 4 on the hole injection layer 3, and the material is N,N'-diphenyl-N,N'-(1-naphthyl)-1,1'-biphenyl-4,4'-diamine (α-NPD) with a thickness of 50 nm, the layer is used as the first hole transport layer 4;

4) vacuum-evaporating a material of the second hole transport layer 5 on the first hole transport layer 4, and the material is 1,3-dicarbazol-9-ylbenzene (mCP) with a thickness of 10 nm, the layer is used as the second hole transport layer 5;

5) co-depositing the light emitting layer 6 on the second hole transport layer 5, and the host material of the light emitting layer 6 is CBP, the guest material is Ir(pyy)3, the mass ratio of the compound CBP to FIrpic is 97:3, and the thickness is 20 nm;

6) vacuum-evaporating the hole blocking layer 7 on the light emitting layer 6, and the material of the hole blocking layer 7 is HB002 prepared in preparation example 1, and the thickness is 5 nm;

7) vacuum-evaporating the electron transport layer 8 on the hole blocking layer 7, and the material of the electron transport layer 8 is BPen, and the thickness is 20 nm;

8) vacuum-evaporating the electron injection layer 9 on the electron transport layer 8, and the material of the electron injection layer 9 is LiF, and the thickness is 1 nm; and 9) vacuum-evaporating the aluminum electrode on the electron injection layer 9 as the cathode 10, and the thickness is 15 nm,

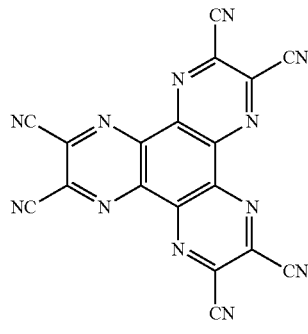

HAT-CN

-continued

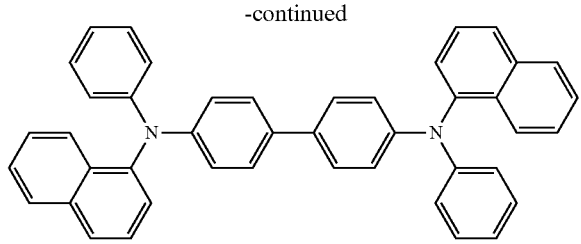
α-NPD

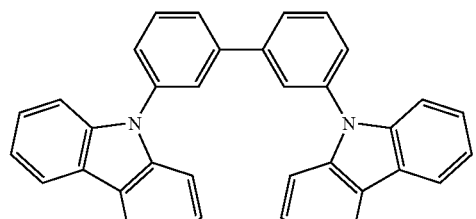
mcp

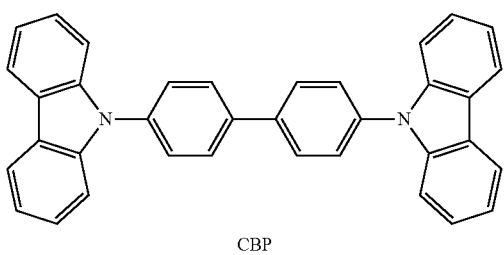
CBP

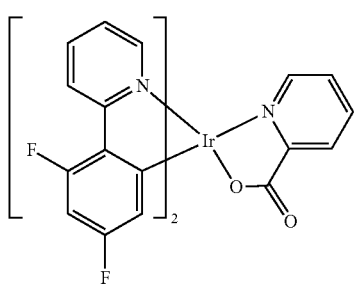
FIrpic

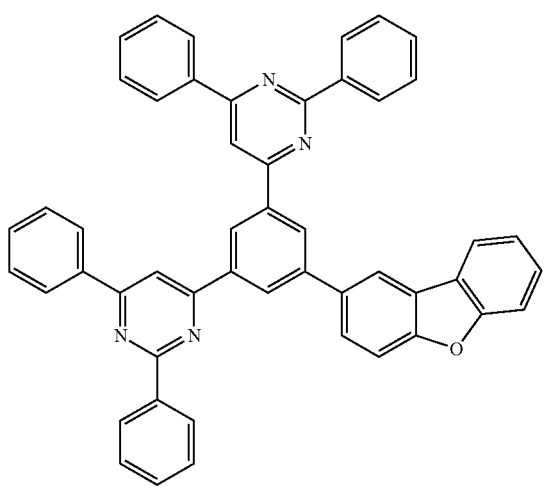
HB002

-continued

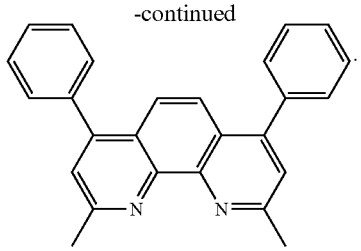
BPen

Example 11

The only difference from Example 10 is that HB002 is replaced with HB042.

Example 12

The only difference from Example 10 is that HB042 is replaced with HB044.

Example 13

The only difference from Example 10 is that HB045 is replaced with HB058.

Example 14

The only difference from Example 10 is that HB050 is replaced with HB063.

Example 15

The only difference from Example 10 is that HB002 is replaced with HB067.

Example 16

The difference from Example 10 is that HB002 is replaced with HB068 which is used as the material of the electron transport layer, and the material of the hole blocking layer is BPen.

Example 17

The difference from Example 10 is that HB002 is replaced with HB069 which is used as the material of the electron transport layer material, and the material of the hole blocking layer is BPen.

Example 18

The difference from Example 10 is that HB002 is replaced with HB072 which is used as the electron transport layer material, and the material of the hole blocking layer is BPen.

Comparative Example 2

The difference from Example 10 is that HB002 is replaced with M.

Comparative Example 3

The difference from Example 16 is that HB068 is replaced with M.

The performance of the organic electroluminescent device is shown in Table 2.

TABLE 2

|  | Hole Blocking Material | Driving Voltage V | Current Efficiency cd/A | Service Life (LT95@50 mA/cm²) |
|---|---|---|---|---|
| Comparative Example 2 | M | 3.78 | 108.2 | 63 |
| Example 10 | HB002 | 3.70 | 125.1 | 75 |
| Example 11 | HB042 | 3.62 | 126.2 | 73 |
| Example 12 | HB044 | 3.69 | 124.8 | 72 |
| Example 13 | HB058 | 3.66 | 123.2 | 75 |
| Example 14 | HB063 | 3.68 | 124.3 | 70 |
| Example 15 | HB067 | 3.64 | 125.4 | 71 |
|  | Electron Transport Material |  |  |  |
| Comparative Example 3 | M | 3.80 | 106.4 | 61 |
| Example 16 | HB068 | 3.62 | 124.3 | 72 |
| Example 17 | HB069 | 3.65 | 123.8 | 71 |
| Example 18 | HB072 | 3.67 | 122.7 | 73 |

As can be seen from Table 2, the OLED display panel provided by the present disclosure has a low driving voltage, high light emitting efficiency and long service life, and the driving voltage is less than 3.70 V, the light emitting efficiency is greater than 120 Cd/A, and the service life is greater than 70 h. Compared with comparative example 2 and comparative example 3, the above performance of the display panel is obviously improved, which is mainly due to the low HOMO value and higher triplet energy level of the material of the present disclosure, which can effectively block the backflow of excitons and prevent holes from crossing the light emitting layer.

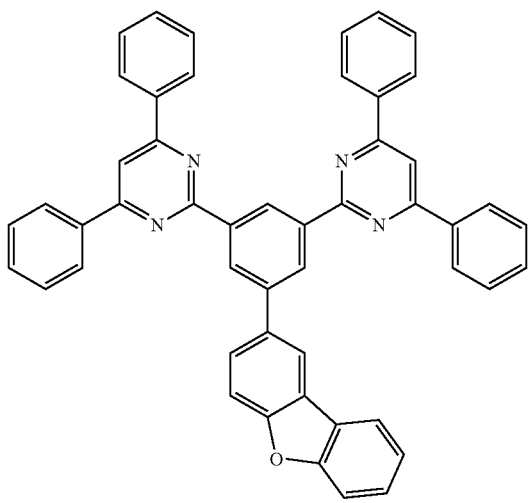

HB004
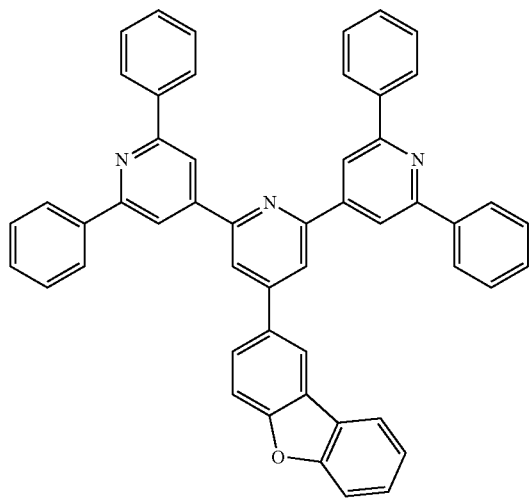
HB007
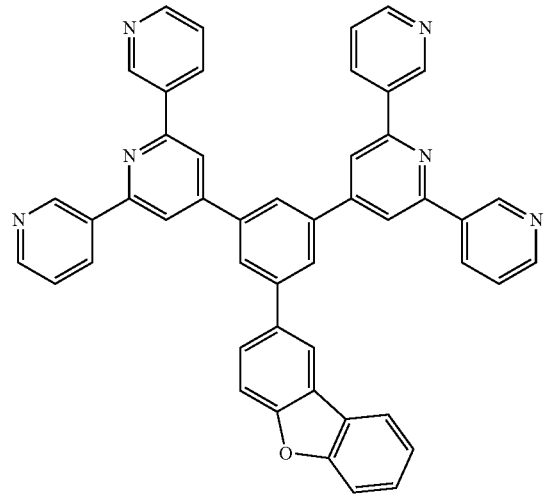
HB005
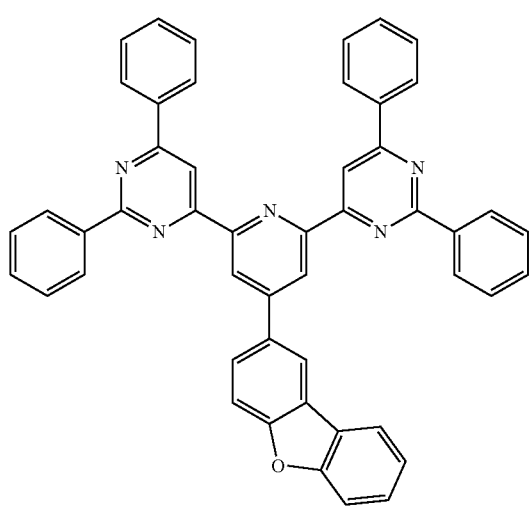
HB008
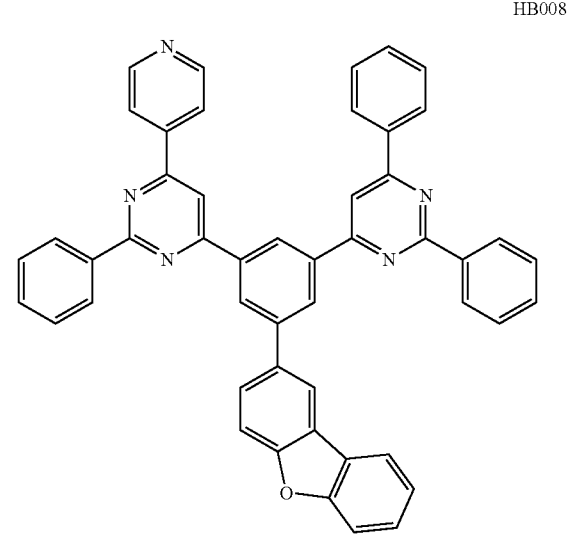
HB006
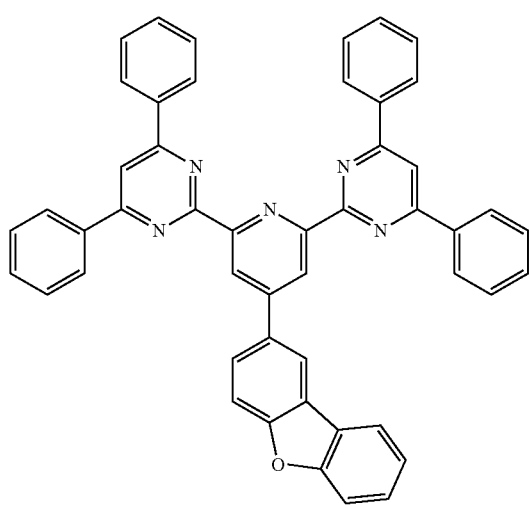
HB009
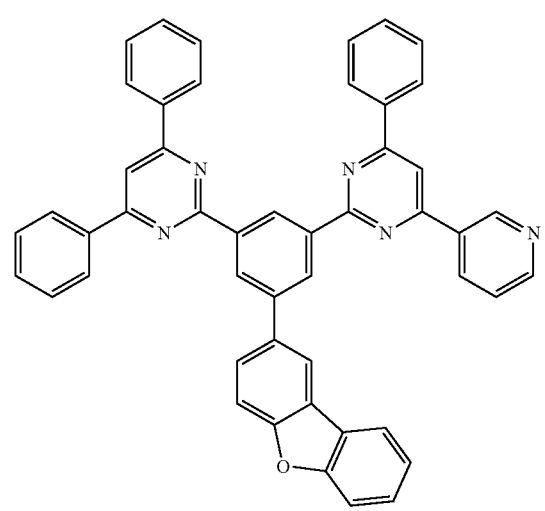

-continued
HB010
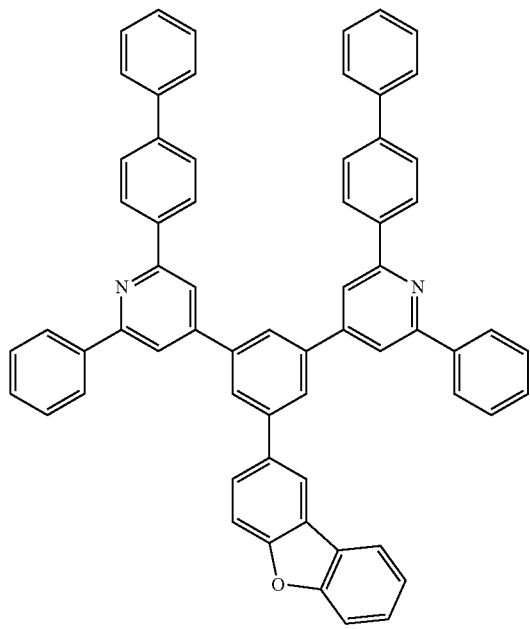
HB011
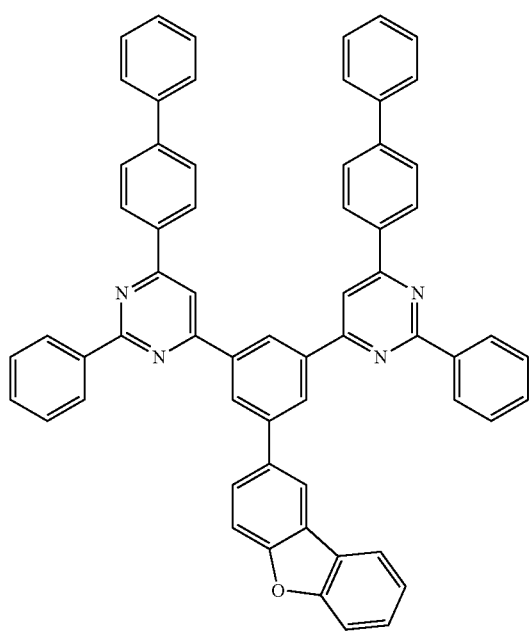
HB012
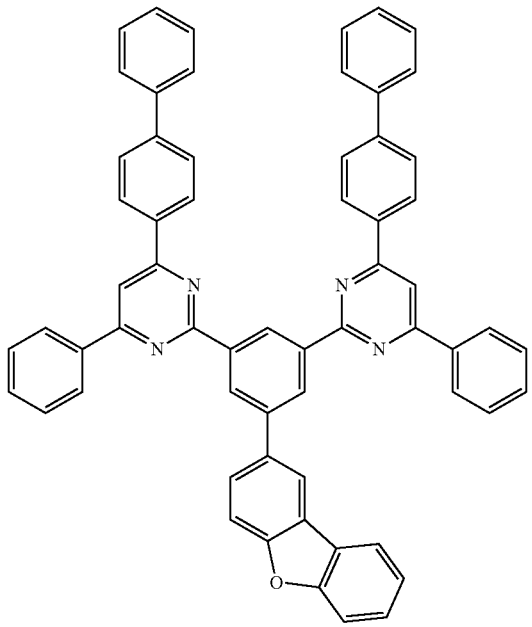
HB013
HB014
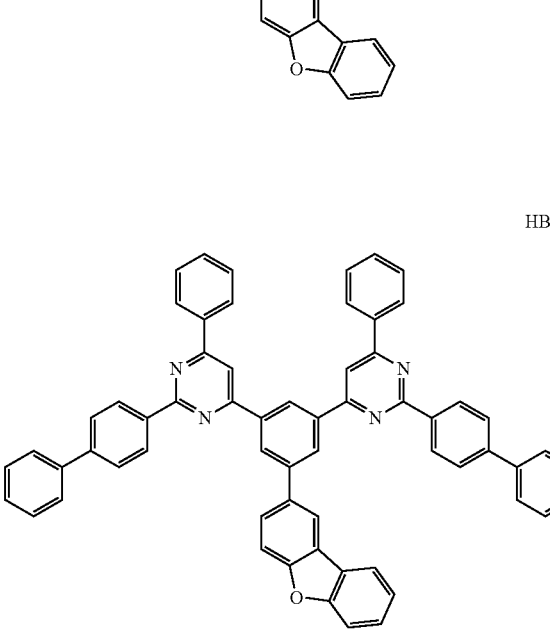

HB015
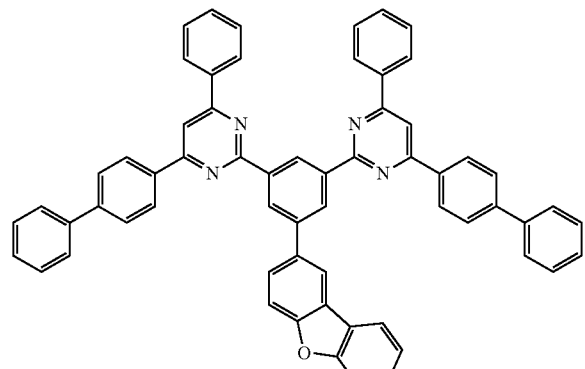
HB016
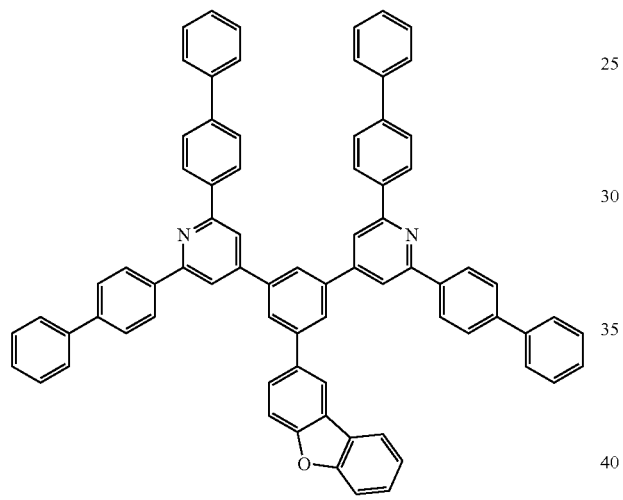
HB017
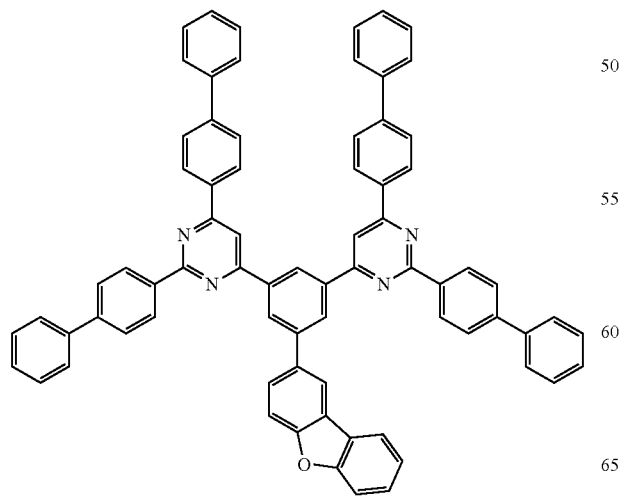
HB018
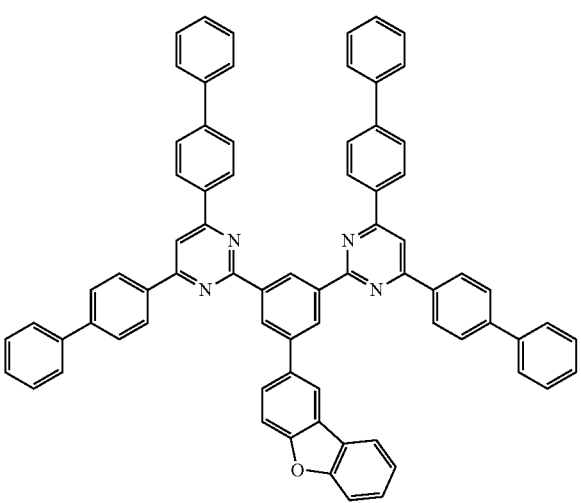
HB019
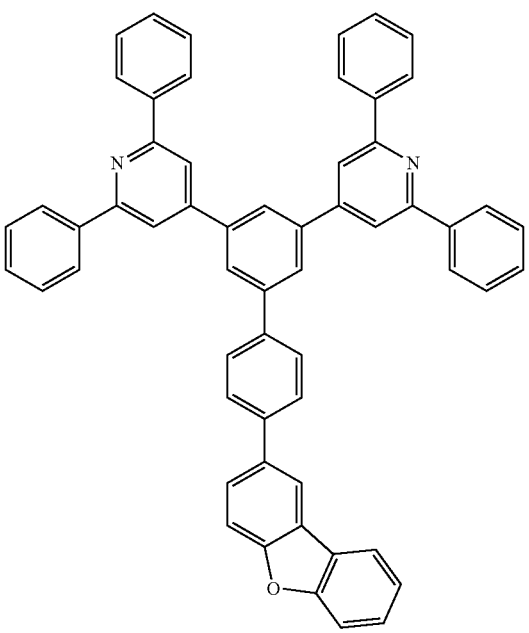

HB020
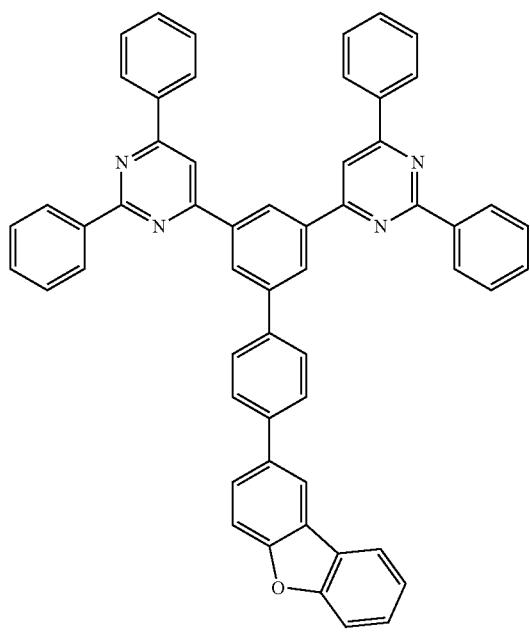
HB021
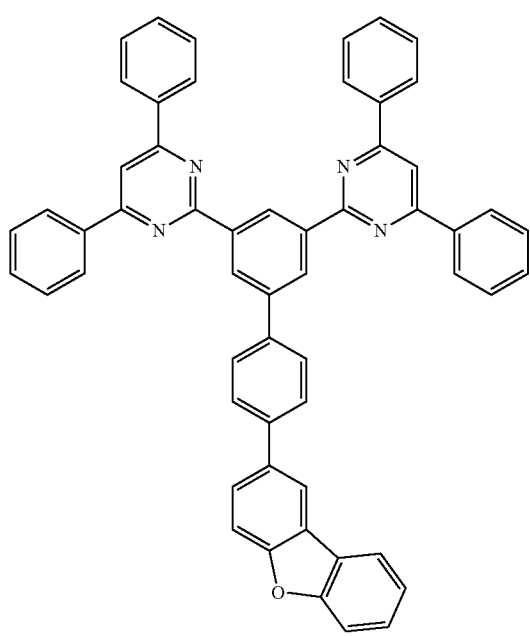
HB022
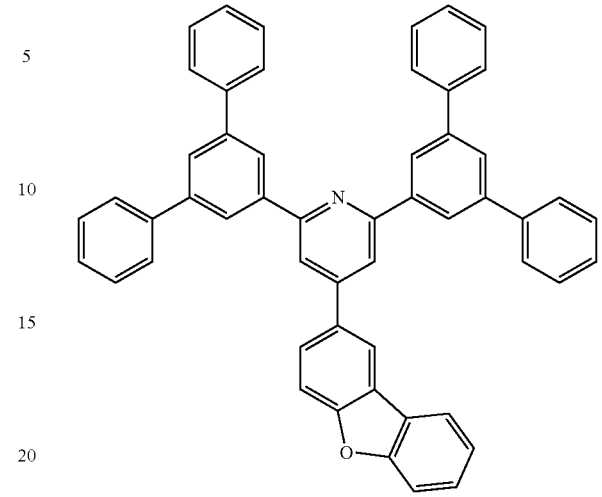
HB023
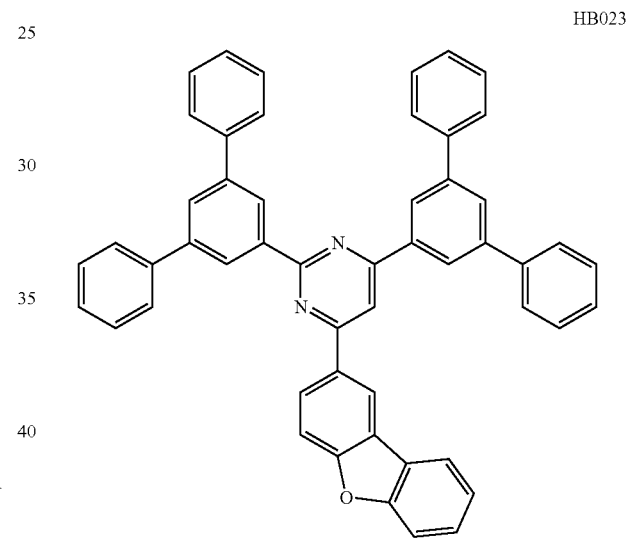
HB024
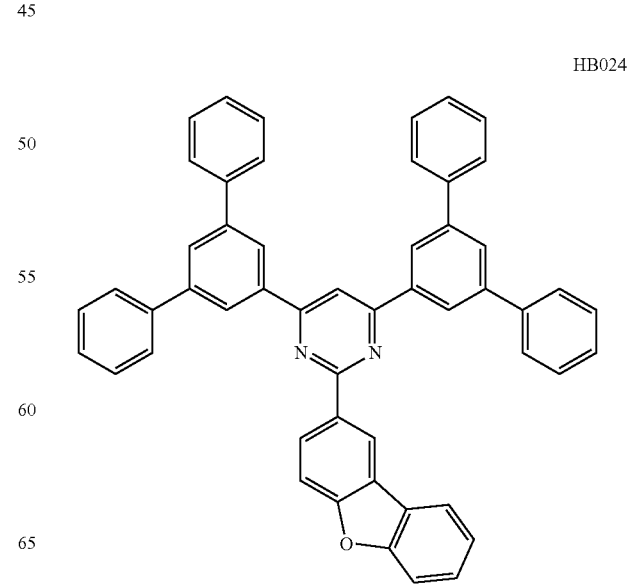

HB025
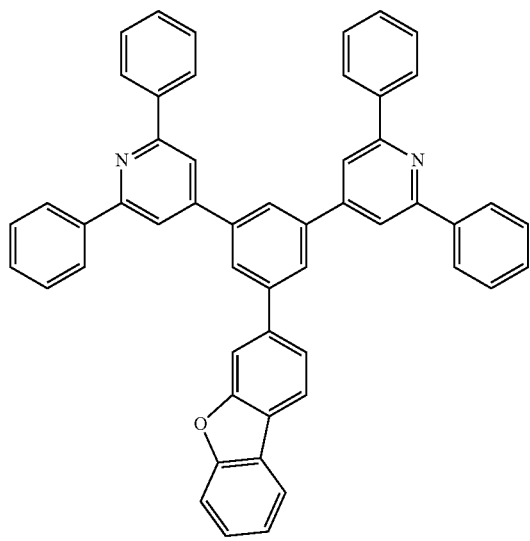
HB026
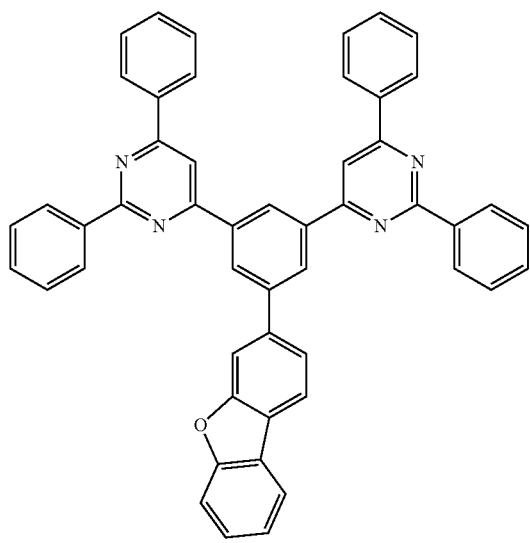
HB027
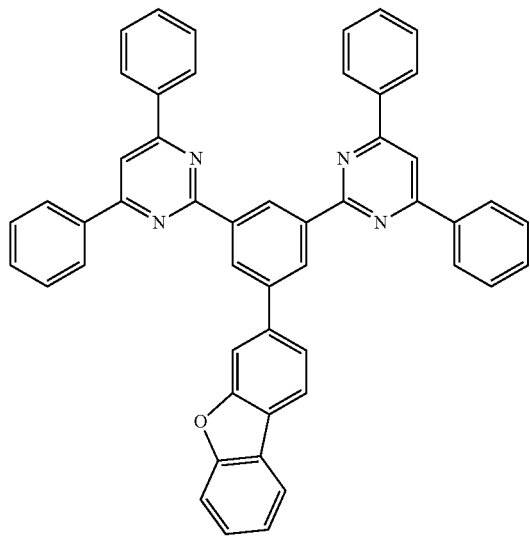
HB028
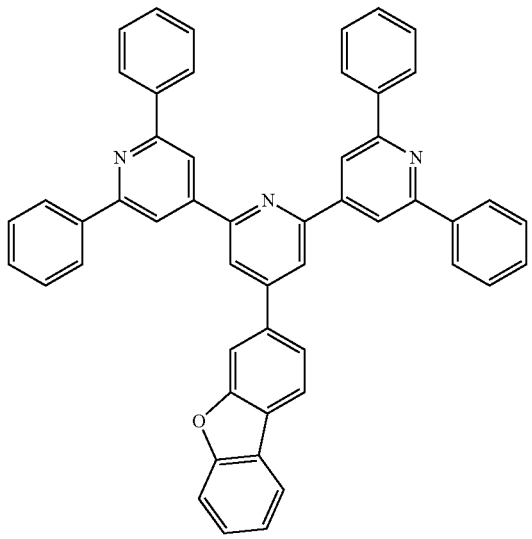
HB029
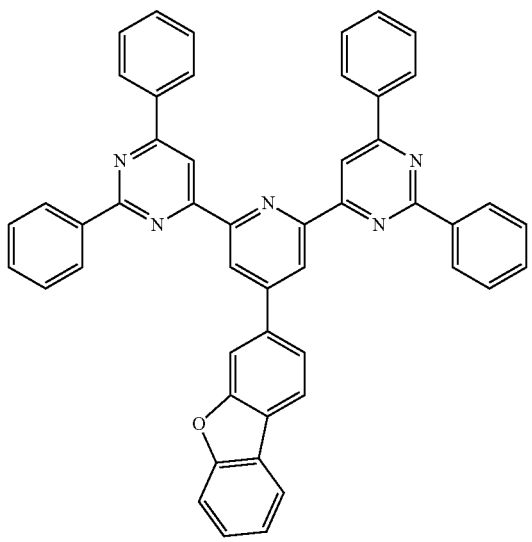
HB030
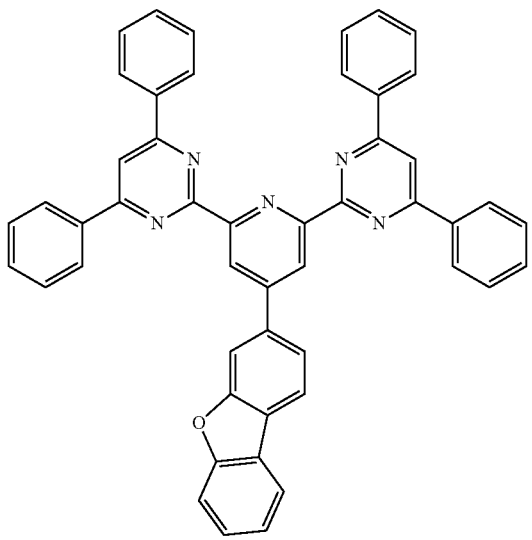

HB031
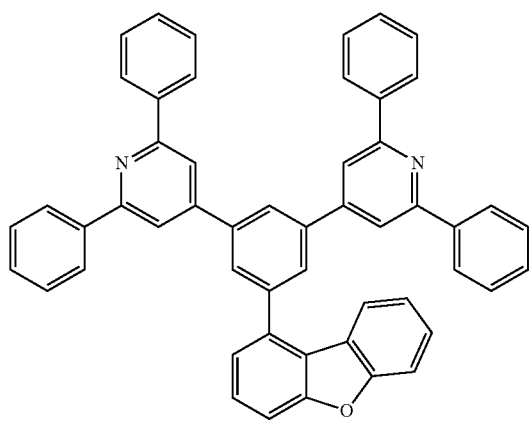
HB034
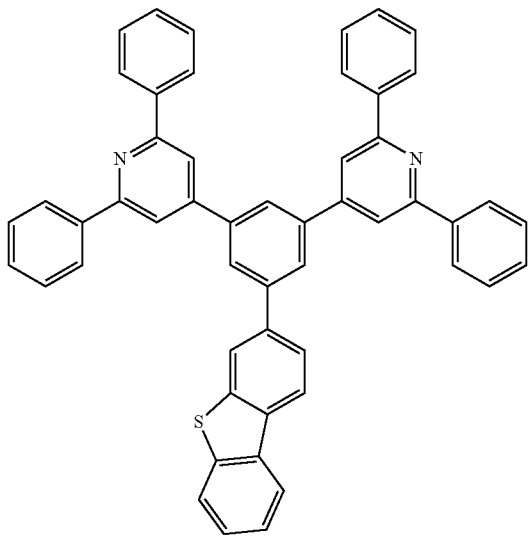
HB032
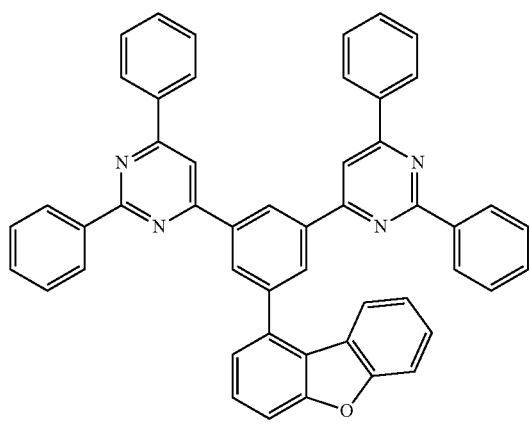
HB035
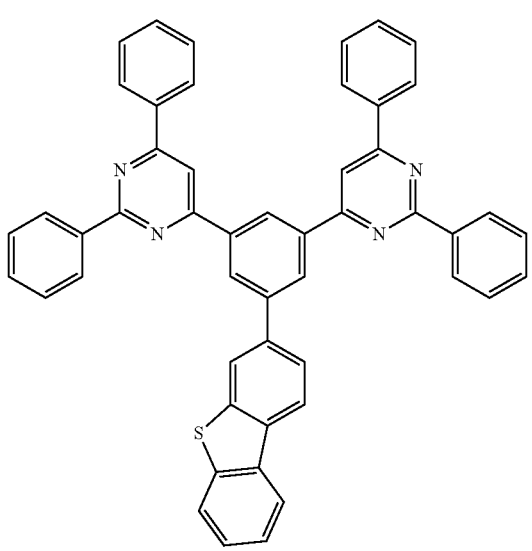
HB033
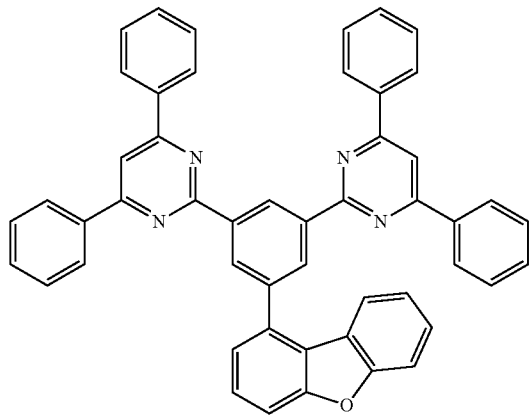
HB036
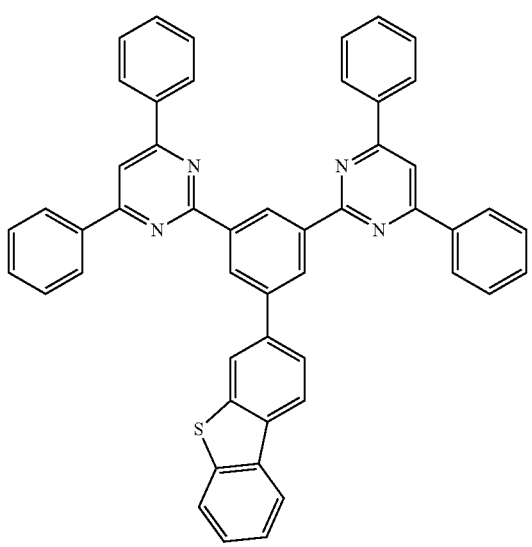

-continued
HB037
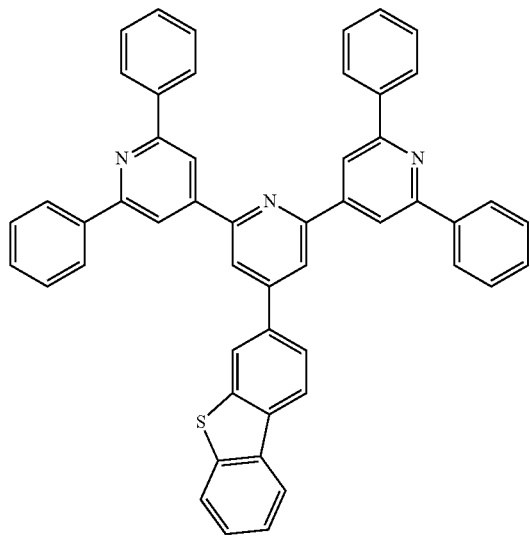
HB038
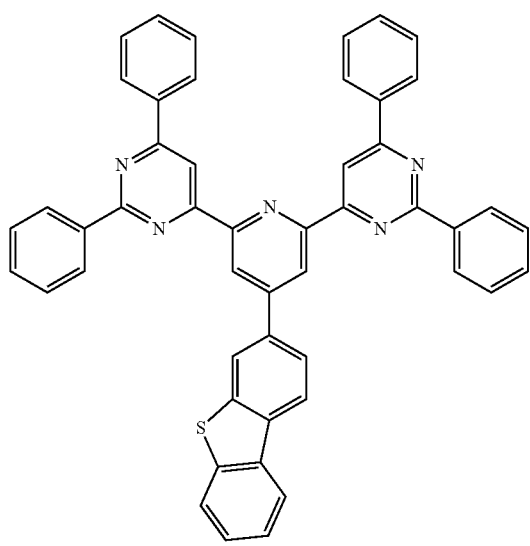
HB039
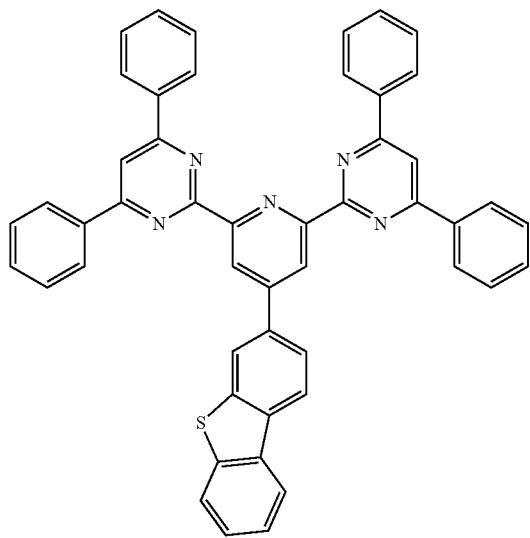
-continued
HB040
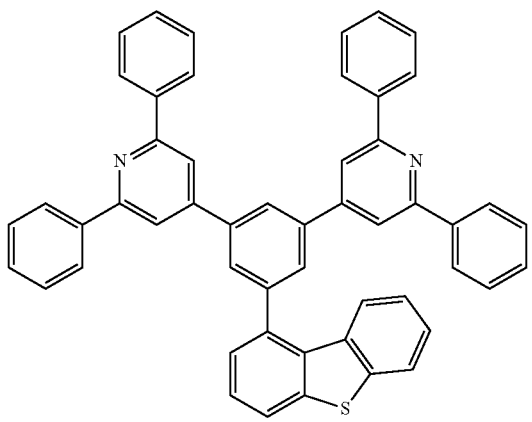
HB041
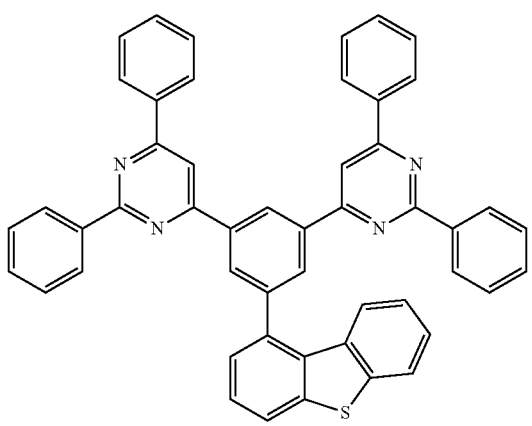
HB042
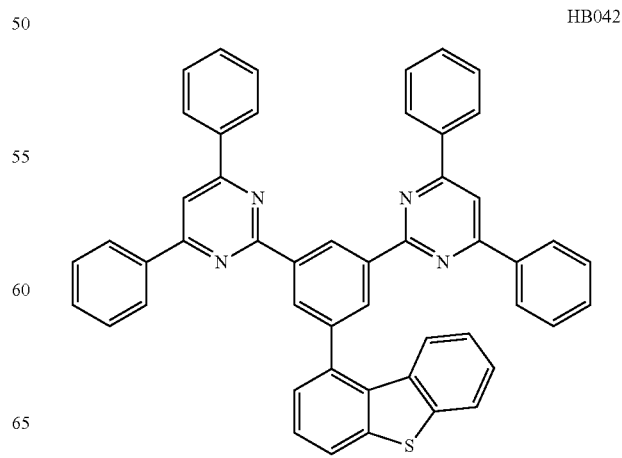

HB043
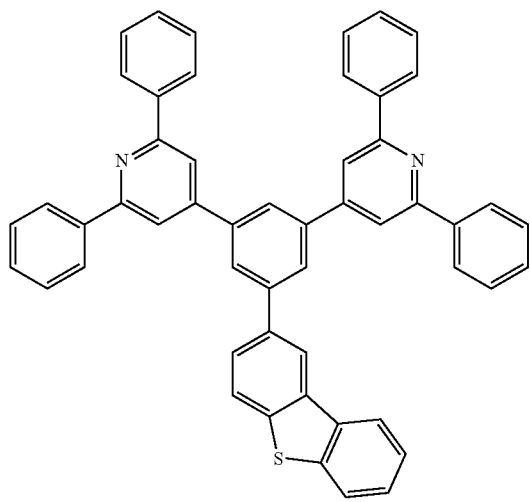
HB046
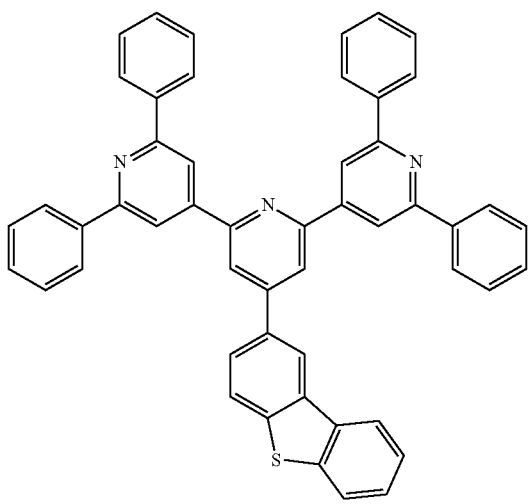
HB044
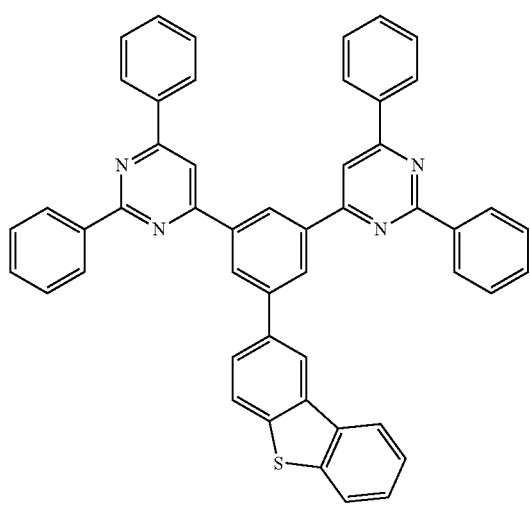
HB047
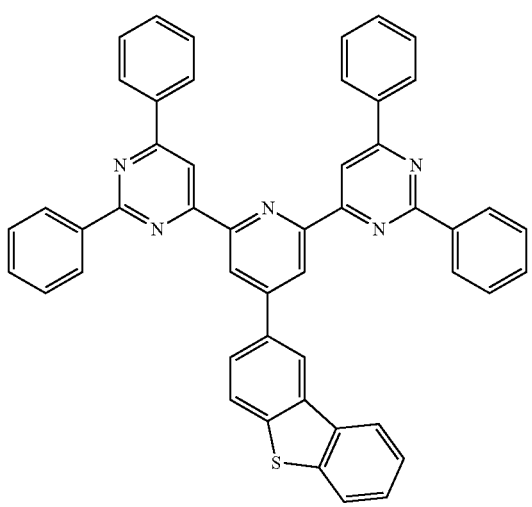
HB045
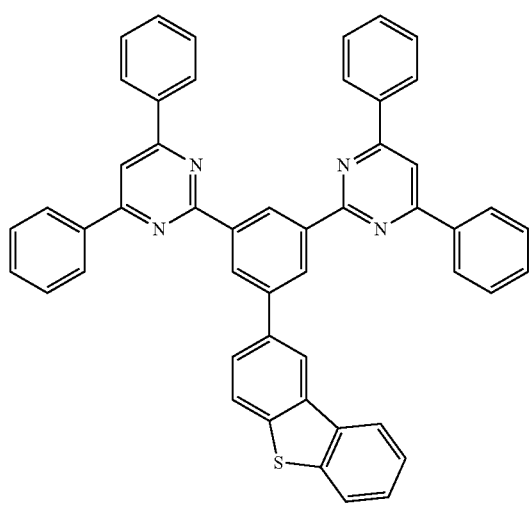
HB048
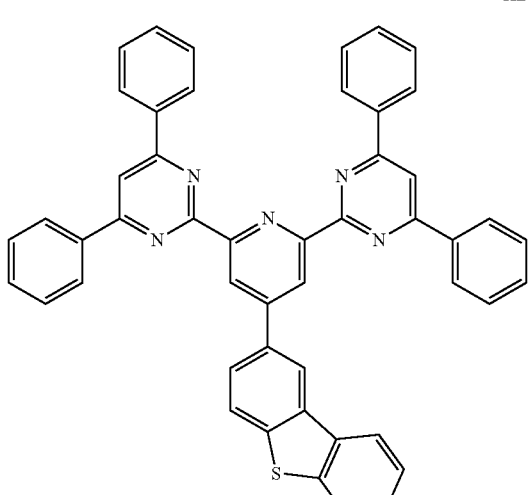

HB049
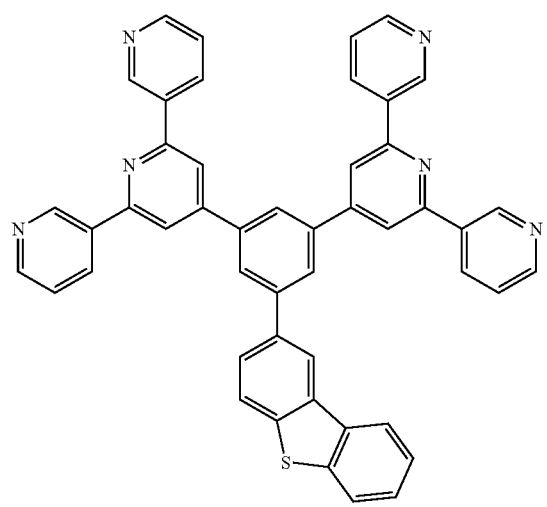
HB050
HB051
HB052
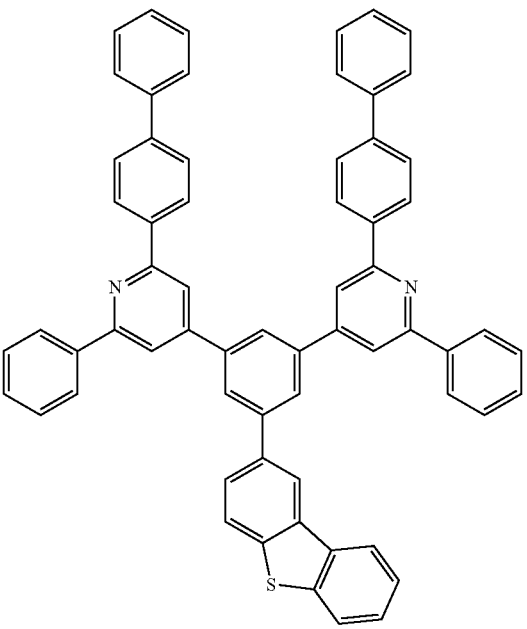
HB053
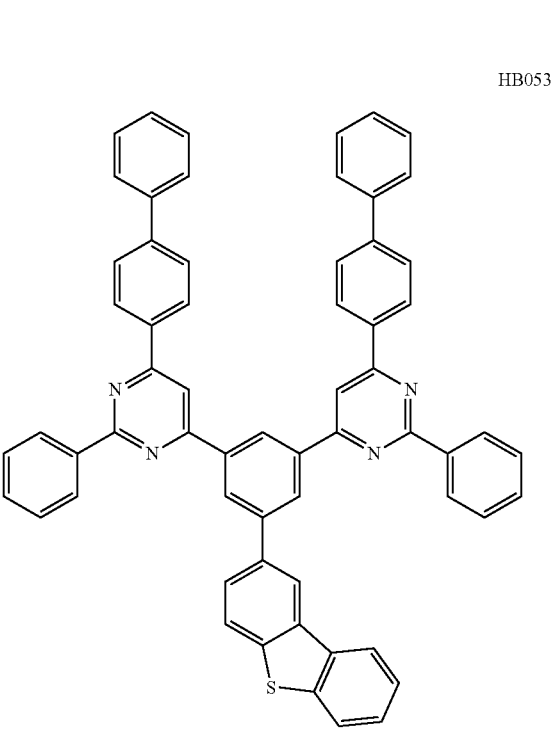

HB054
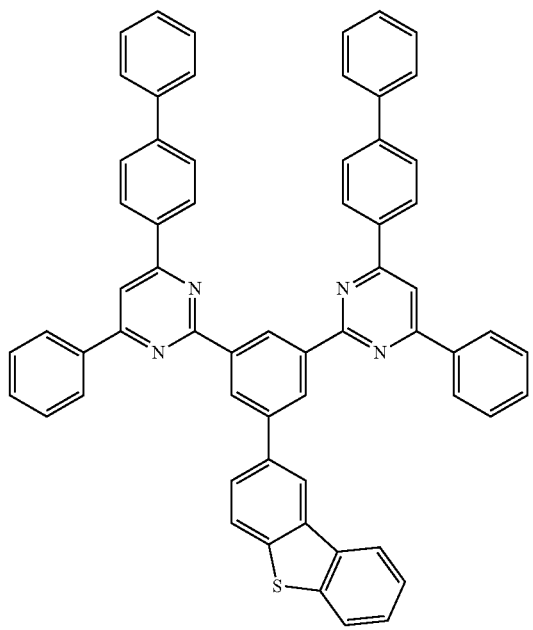
HB056
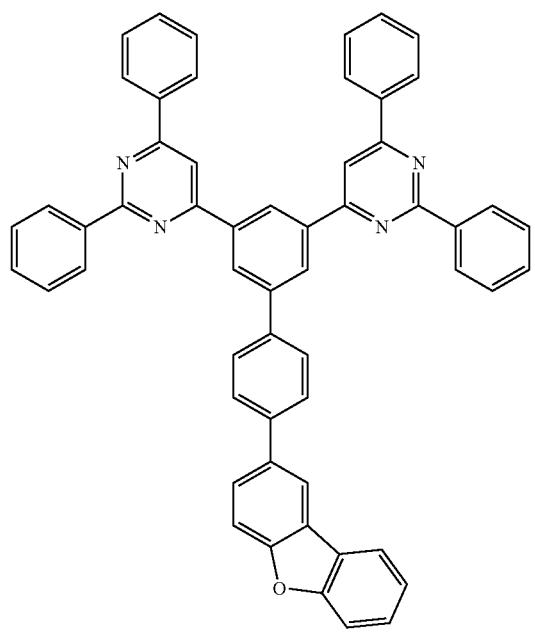
HB055
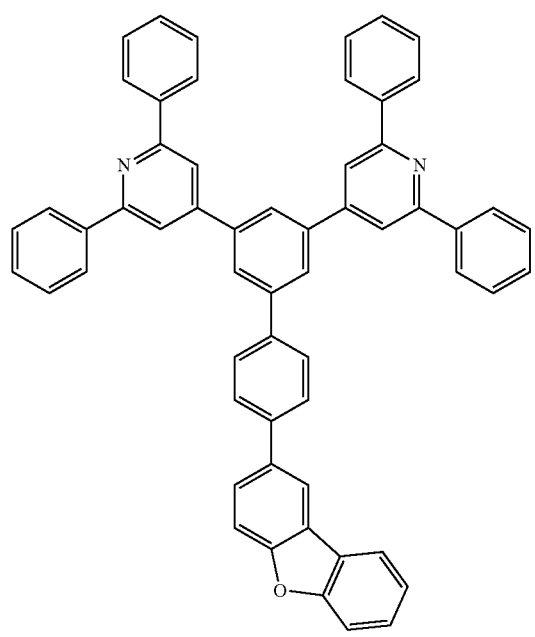
HB057
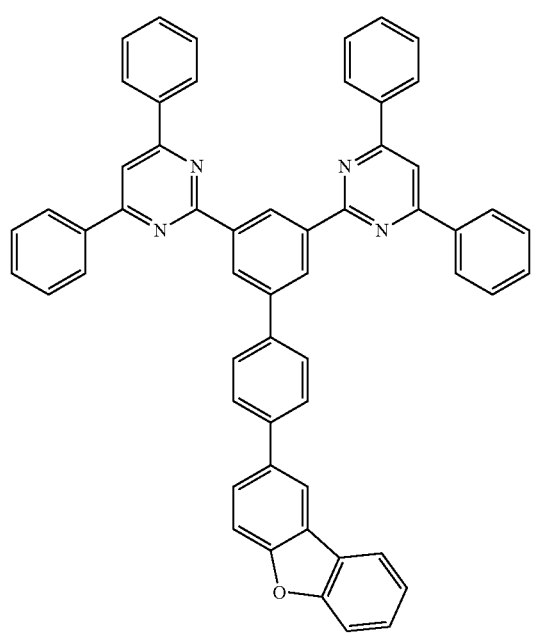

HB058
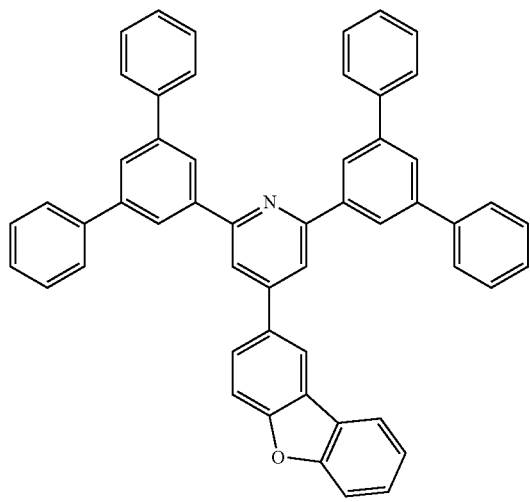
HB061
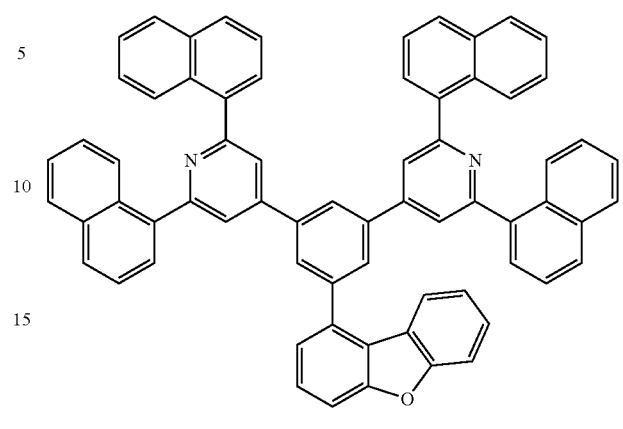
HB059
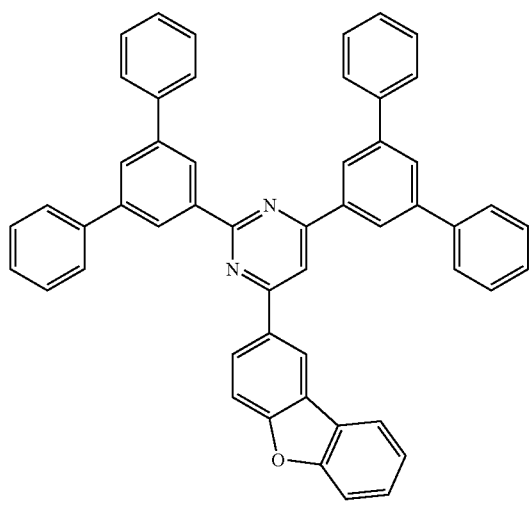
HB062
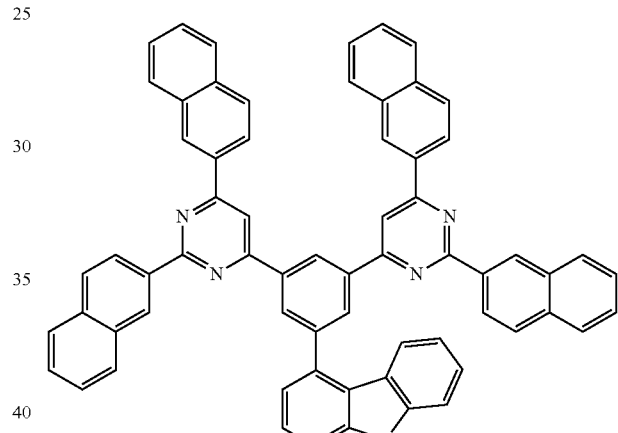
HB060
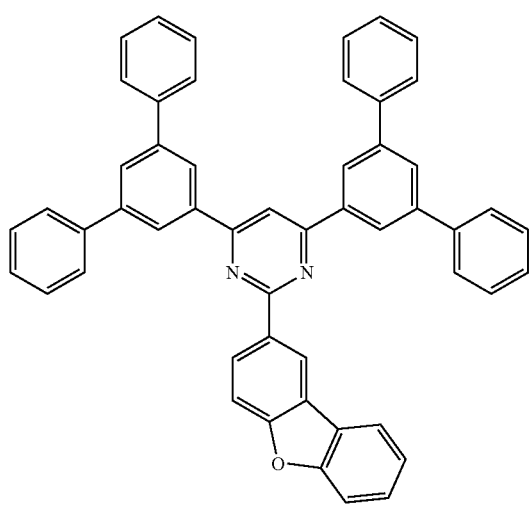
HB063
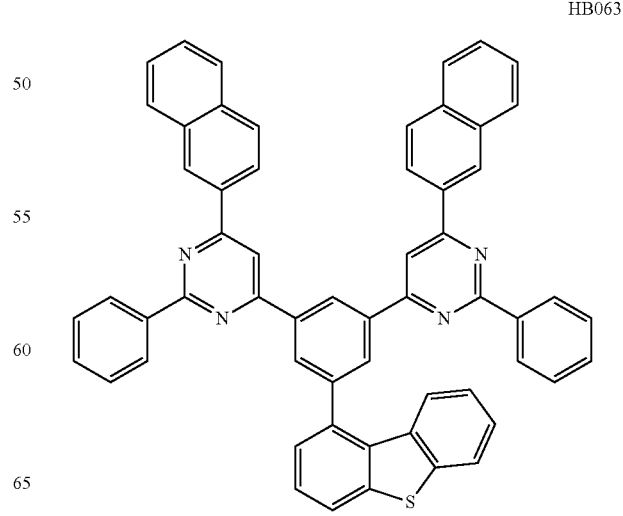

HB064
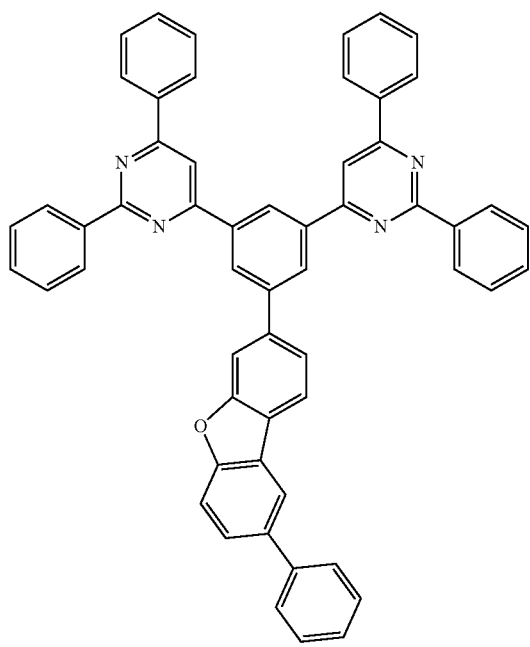
HB066
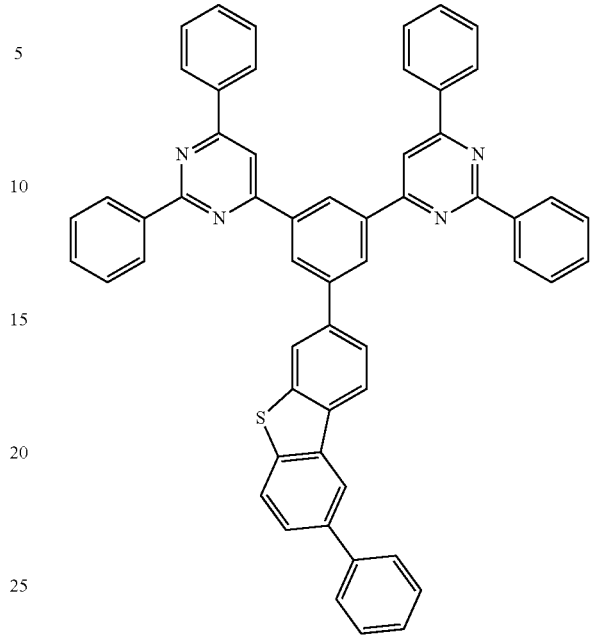
HB065
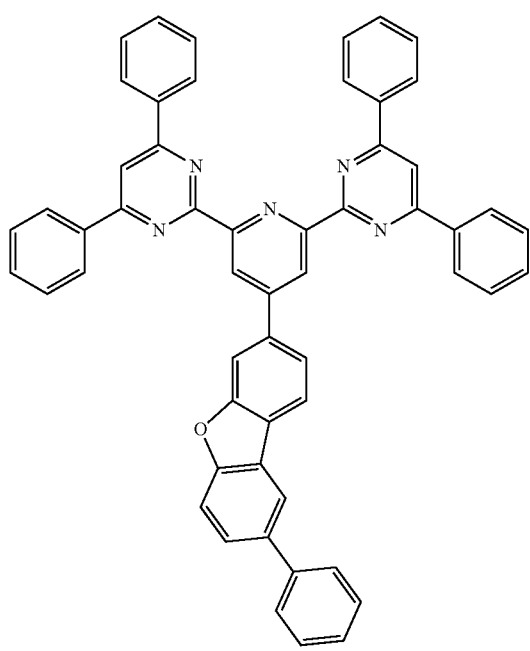
BH067
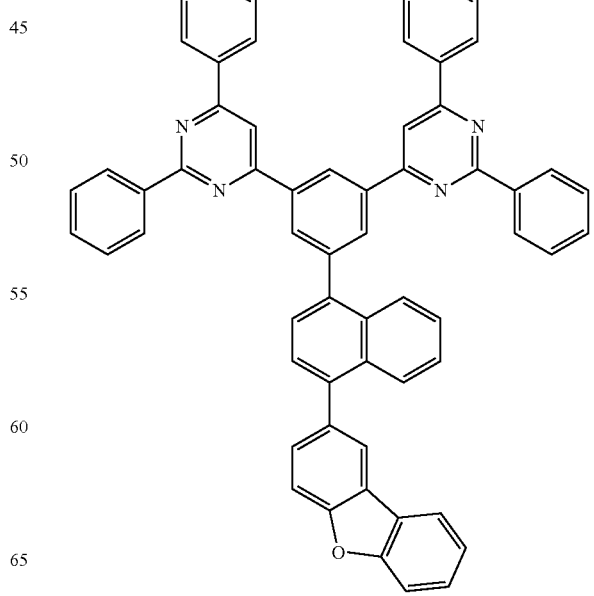

HB068
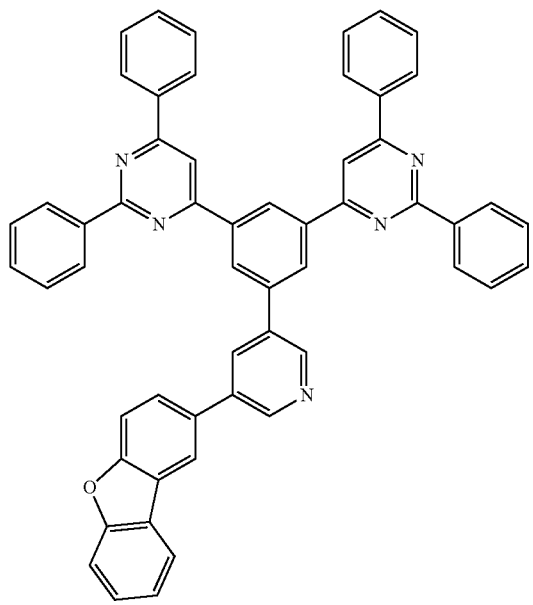
HB070
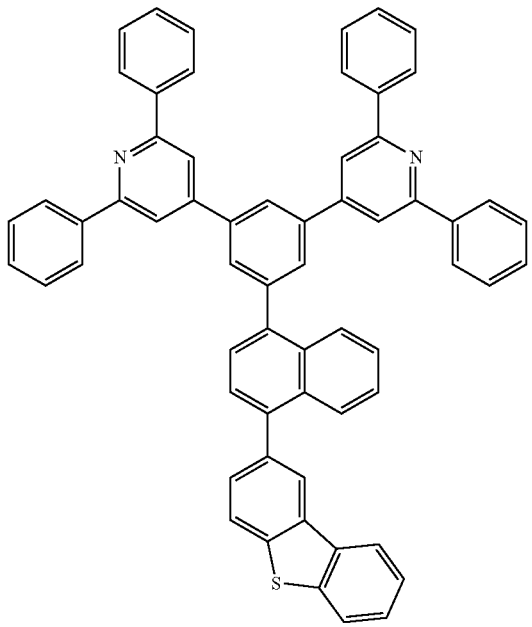
HB069
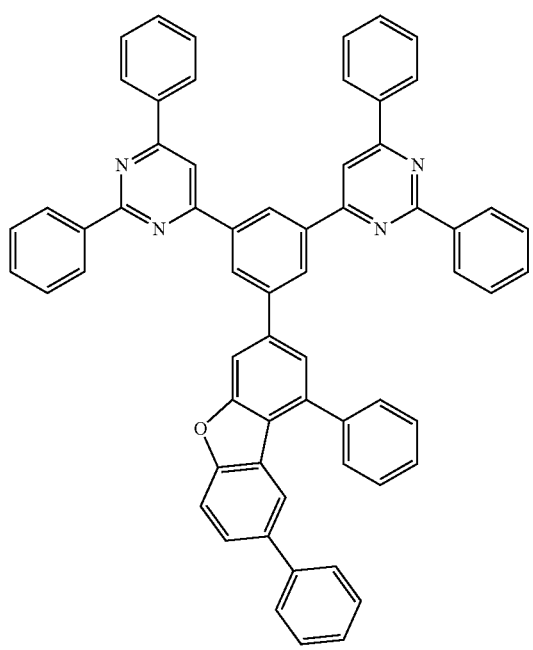
HB071
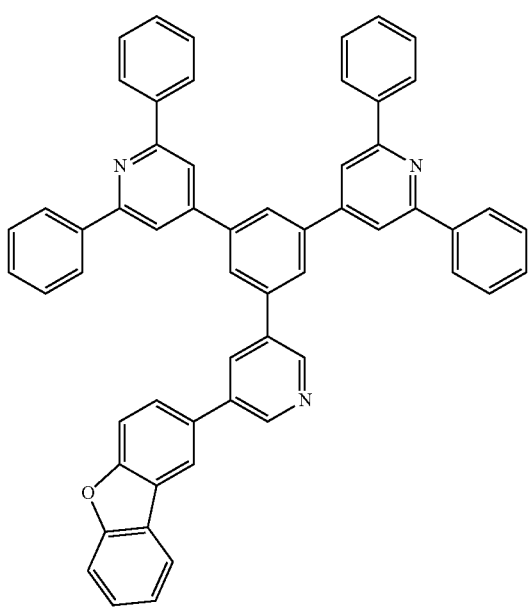

HB072
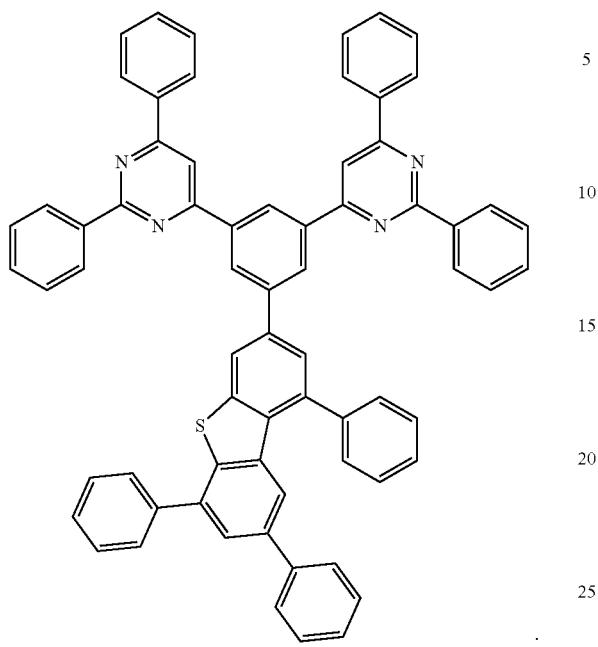

What is claimed is:

1. A compound, comprising a structure as shown in Formula (I),

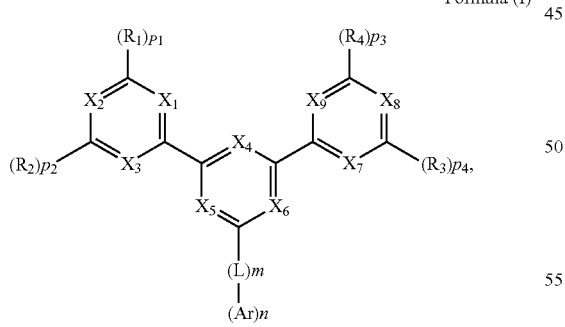

Formula (I)

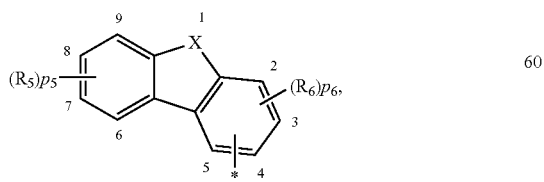

Formula (II)

wherein $X_1$-$X_9$ are each independently a C or N atom;
wherein among $X_1$-$X_3$ and $X_7$-$X_9$, $X_2$, $X_3$, $X_7$, and $X_8$ are N atoms, and $X_1$, $X_9$ are C atoms; L is selected from substituted or unsubstituted C5-C40 aryl, and substituted or unsubstituted C3-C40 heteroaryl;

Ar is Formula (II), wherein X is selected from an O or S atom;

$R_1$-$R_6$ are each independently selected from substituted or unsubstituted C5-C40 aryl, and substituted or unsubstituted C3-C40 heteroaryl;

$p_1$-$p_4$ are each independently selected from 0 or 1; $p_5$-$p_6$ are each independently selected from 0, 1, 2, or 3;

m is selected from 0, 1, 2, or 3; n is selected from 1, 2, or 3; and

* represents a connection site.

2. The compound according to claim 1, wherein $X_1$ and $X_9$ are identical, $X_2$ and $X_8$ are identical, and $X_3$ and $X_7$ are identical.

3. The compound according to claim 1, wherein among $X_4$-$X_6$, $X_4$ is an N atom, and $X_5$ and $X_6$ are C atoms.

4. The compound according to claim 1, wherein among $X_4$-$X_6$, $X_4$ and $X_5$ are N atoms, and $X_6$ is a C atom.

5. The compound according to claim 1, wherein among $X_4$-$X_6$, $X_5$ and $X_6$ are N atoms, and $X_4$ is a C atom.

6. The compound according to claim 1, wherein L is selected from any one of:

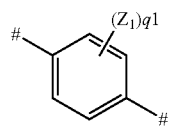

chemical formular 2-1

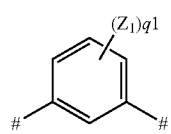

chemical formular 2-2

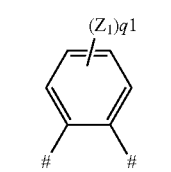

chemical formular 2-3

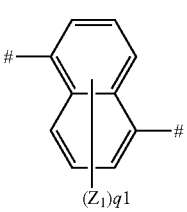

chemical formular 2-4

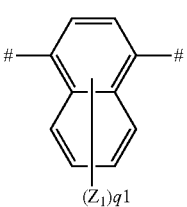

chemical formular 2-5

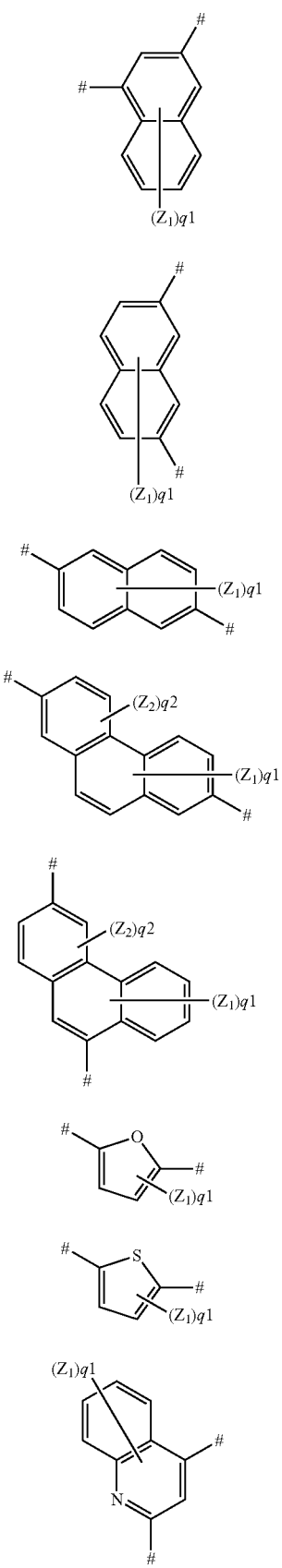
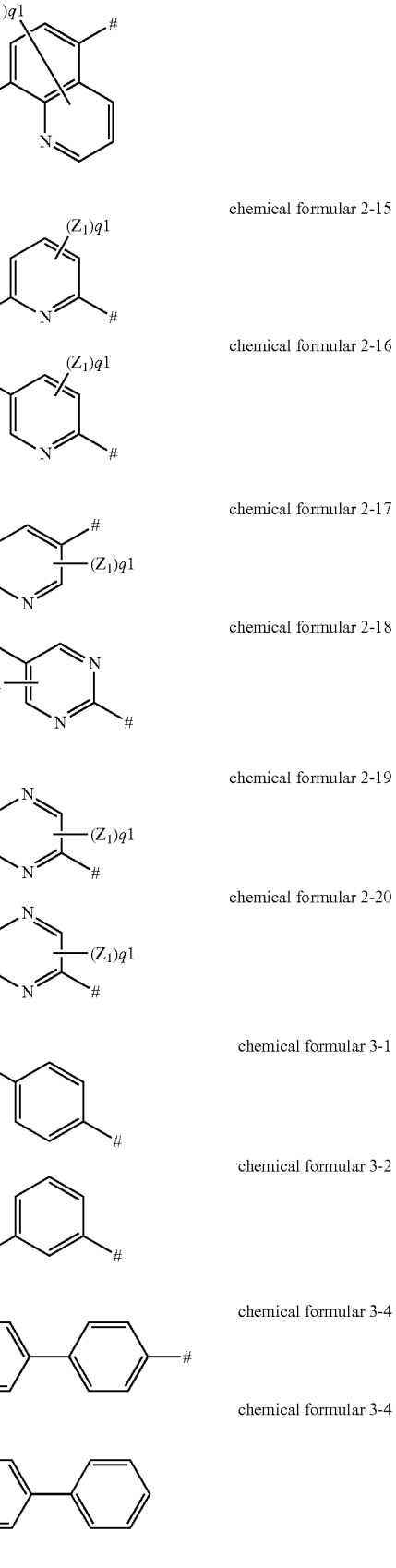

chemical formular 3-5 chemical formular 3-6 chemical formular 3-7 chemical formular 3-8 chemical formular 3-9 chemical formular 3-10 chemical formular 3-11 chemical formular 3-12 chemical formular 3-13 chemical formular 3-14 chemical formular 3-15 chemical formular 3-16

Z1 is selected from substituted or unsubstituted C5-C40 aryl, and substituted or unsubstituted C3-C40 heteroaryl;

q1 and q2 are each independently selected from 0, 1, or 2; and # represents a connection site.

7. The compound according to claim 1, wherein the Formula (II) is selected from any one of

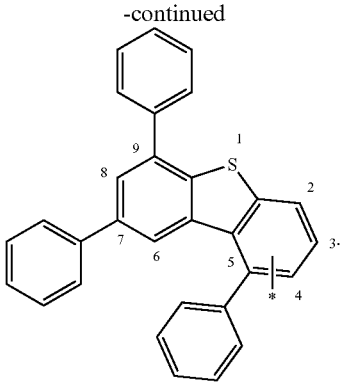

8. The compound according to claim 1, wherein the Formula (II) is selected from any one of

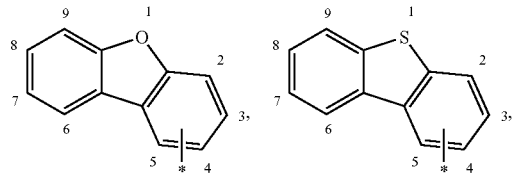

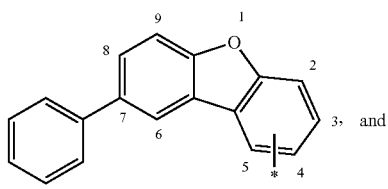

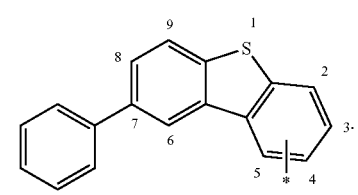

9. The compound according to claim 1, wherein the connection site * in the Formula (II) is a position of a No. 3 carbon atom, a No. 4 carbon atom, a No. 5 carbon atom, a No. 6 carbon atom, a No. 7 carbon atom or a No. 8 carbon atom.

10. An organic electroluminescent device, comprising a first electrode, a second electrode, and an organic functional layer located between the first electrode and the second electrode, the organic functional layer comprises an electron transport layer, wherein an electron transport material of the electron transport layer comprises the compound according to claim 1.

11. The organic electroluminescent device according to claim 10, wherein the organic functional layer further comprises a hole blocking layer, and an electron transport material of the hole blocking layer comprises the compound according to claim 1.

12. A display device, comprising the organic electroluminescent device according to claim 10.

13. A compound, comprising a structure as shown in Formula (I),

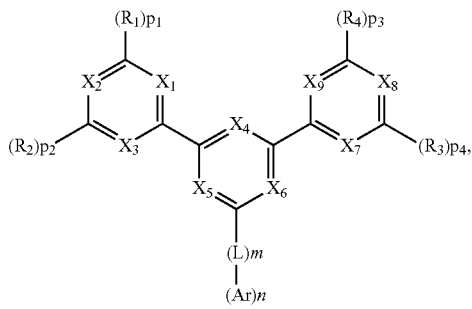

Formula (I)

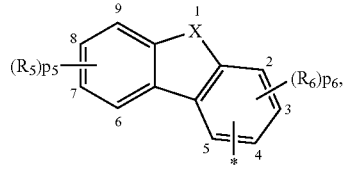

Formula (II)

wherein $X_1$-$X_9$ are each independently a C or N atom; L is selected from substituted or unsubstituted C5-C40 aryl, and substituted or unsubstituted C3-C40 heteroaryl;

Ar is Formula (II), wherein X is selected from an O or S atom;

$R_1$-$R_6$ are each independently selected from substituted or unsubstituted C5-C40 aryl, and substituted or unsubstituted C3-C40 heteroaryl;

$p_1$-$p_4$ are each independently selected from 0 or 1; $p_5$-$p_6$ are each independently selected from 0, 1, 2, or 3;

m is selected from 0, 1, 2, or 3; n is selected from 1, 2, or 3; and

* represents a connection site;

wherein among $X_1$-$X_3$ and $X_7$-$X_9$, $X_2$ and $X_8$ are N atoms, and $X_1$, $X_3$, $X_7$, $X_9$ are C atoms, and among $X_4$-$X_6$, $X_4$ is an N atom, and $X_5$ and $X_6$ are C atoms, or among $X_1$-$X_3$ and $X_7$-$X_9$, $X_2$ and $X_8$ are N atoms, and $X_1$, $X_3$, $X_7$, $X_9$ are C atoms, and among $X_4$-$X_6$, $X_4$ and $X_5$ are N atoms, and $X_6$ is a C atom, or among $X_1$-$X_3$ and $X_7$-$X_9$, $X_2$ and $X_8$ are N atoms, and $X_1$, $X_3$, $X_7$, $X_9$ are C atoms, and among $X_4$-$X_6$, $X_5$ and $X_6$ are N atoms, and $X_4$ is a C atom.

14. A compound, comprising a structure as shown in Formula (I),

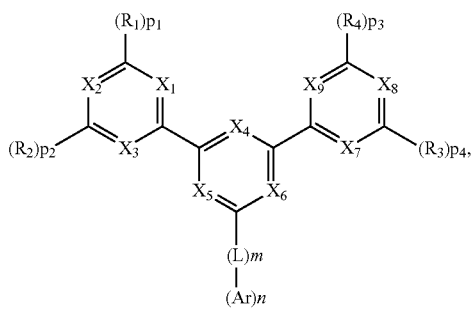

Formula (I)

-continued

Formula (II)

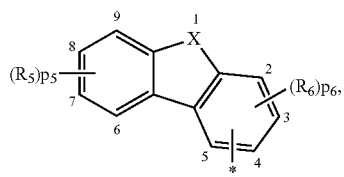

wherein $X_1$-$X_9$ are each independently a C or N atom; L is selected from substituted or unsubstituted C5-C40 aryl, and substituted or unsubstituted C3-C40 heteroaryl;
Ar is Formula (II), wherein X is selected from an O or S atom;
$R_1$-$R_6$ are each independently selected from substituted or unsubstituted C5-C40 aryl, and substituted or unsubstituted C3-C40 heteroaryl;
$p_1$-$p_4$ are each independently selected from 0 or 1; $p_5$-$p_6$ are each independently selected from 0, 1, 2, or 3;
m is selected from 0, 1, 2, or 3; n is selected from 1, 2, or 3; and
* represents a connection site;
wherein among $X_1$-$X_3$ and $X_7$-$X_9$, $X_1$, $X_3$, $X_7$, and $X_9$ are N atoms, and among $X_4$-$X_6$, $X_4$ is an N atom, and $X_5$ and $X_6$ are C atoms,
or
among $X_1$-$X_3$ and $X_7$-$X_9$, $X_1$, $X_3$, $X_7$, and $X_9$ are N atoms, and among $X_4$-$X_6$, $X_4$ and $X_5$ are N atoms, and $X_6$ is a C atom.

15. A compound, comprising a structure as shown in Formula (I),

Formula (I)

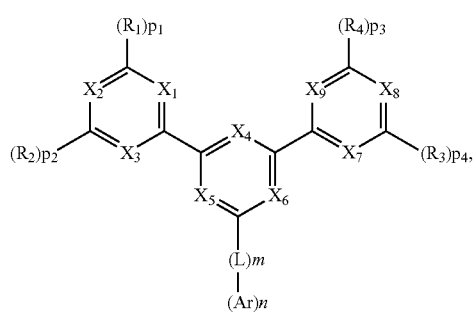

Formula (II)

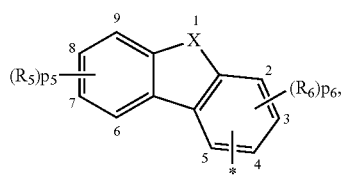

wherein $X_1$-$X_9$ are each independently a C or N atom, and at least one of $X_1$-$X_9$ is an N atom; L is selected from substituted or unsubstituted C5-C40 aryl, and substituted or unsubstituted C3-C40 heteroaryl;
Ar is Formula (II), wherein X is selected from an O or S atom;
$R_1$-$R_6$ are each independently selected from substituted or unsubstituted C5-C40 aryl, and substituted or unsubstituted C3-C40 heteroaryl;
$p_1$-$p_4$ are each independently selected from 0 or 1; $p_5$-$p_6$ are each independently selected from 0, 1, 2, or 3;
m is selected from 0, 1, 2, or 3; n is selected from 1, 2, or 3; and

* represents a connection site; wherein the compound is selected from any one of:

HB001

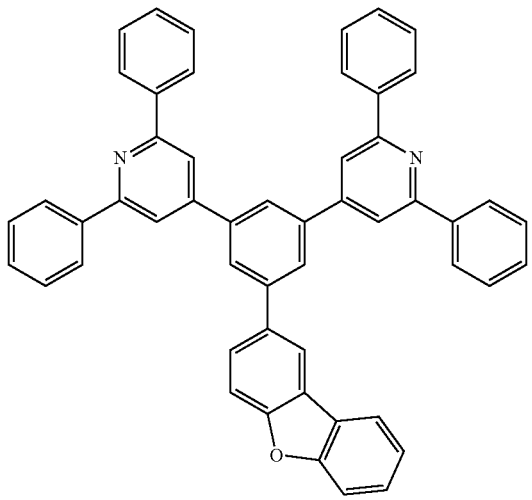

HB002

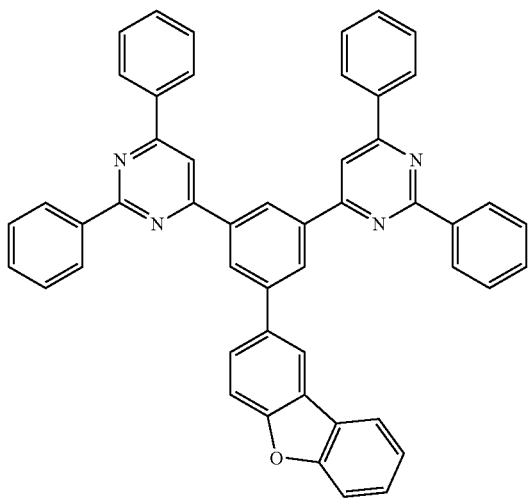

HB003